(12) United States Patent
Miyata

(10) Patent No.: US 9,843,005 B2
(45) Date of Patent: Dec. 12, 2017

(54) AMINE DERIVATIVE, AND ORGANIC ELECTROLUMINESCENCE MATERIAL AND ORGANIC ELECTROLUMINESCENCE DEVICE USING THE SAME

(71) Applicant: SAMSUNG DISPLAY CO., LTD., Yongin, Gyeonggi-Do (KR)

(72) Inventor: Yasuo Miyata, Yongin (KR)

(73) Assignee: Samsung Display Co., Ltd., Yongin, Gyunggi-do (KR)

( * ) Notice: Subject to any disclaimer, the term of this patent is extended or adjusted under 35 U.S.C. 154(b) by 295 days.

(21) Appl. No.: 14/096,188

(22) Filed: Dec. 4, 2013

(65) Prior Publication Data

US 2014/0151666 A1 Jun. 5, 2014

(30) Foreign Application Priority Data

Dec. 5, 2012 (JP) .................. 2012-266773

(51) Int. Cl.
*H01L 51/50* (2006.01)
*H01L 51/00* (2006.01)
(Continued)

(52) U.S. Cl.
CPC ........ *H01L 51/0094* (2013.01); *C07F 7/0812* (2013.01); *C07F 7/0814* (2013.01); *C07F 7/0816* (2013.01); *C07F 7/0818* (2013.01); *C07F 9/65685* (2013.01); *C09K 11/06* (2013.01); *H01L 51/006* (2013.01); *H01L 51/0059* (2013.01); *H01L 51/0061* (2013.01); *H01L 51/0072* (2013.01); *H01L 51/0074* (2013.01); *C09K 2211/1007* (2013.01); *C09K 2211/1011* (2013.01); *C09K 2211/1025* (2013.01); *C09K 2211/1029* (2013.01); *C09K 2211/1033* (2013.01); *C09K 2211/1088* (2013.01); *C09K 2211/1092* (2013.01); *H01L 51/0052* (2013.01); *H01L 51/0054* (2013.01); *H01L 51/0058* (2013.01); *H01L 51/0067* (2013.01); *H01L 51/0068* (2013.01); *H01L 51/0073* (2013.01); *H01L 51/5012* (2013.01);
(Continued)

(58) Field of Classification Search
None
See application file for complete search history.

(56) References Cited

U.S. PATENT DOCUMENTS 5,187,310 A 2/1993 Mishima et al.
2005/0234256 A1 10/2005 Marks et al.
(Continued)

FOREIGN PATENT DOCUMENTS

CN 102190627 A 9/2011
JP H-05323634 A 12/1993
(Continued)

Primary Examiner — Gregory Clark
(74) Attorney, Agent, or Firm — Lee & Morse, P.C.

(57) ABSTRACT

An amine derivative represented by compound (1) of following Formula 1:

[Formula 1]

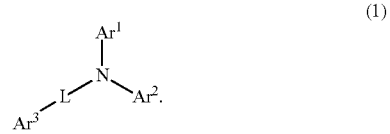

(1)

7 Claims, 2 Drawing Sheets

(51) Int. Cl.
*C07F 9/6568* (2006.01)
*C07F 7/08* (2006.01)
*C09K 11/06* (2006.01)
*H01L 51/52* (2006.01)

(52) U.S. Cl.
CPC ...... *H01L 51/5056* (2013.01); *H01L 51/5206* (2013.01)

(56) References Cited

U.S. PATENT DOCUMENTS

| | | | | |
|---|---|---|---|---|
| 2007/0205715 | A1* | 9/2007 | Saitoh | C07F 7/0812 |
| | | | | 313/504 |
| 2007/0231503 | A1 | 10/2007 | Hwang et al. | |
| 2010/0001636 | A1* | 1/2010 | Yabunouchi | C07D 307/91 |
| | | | | 313/504 |
| 2011/0031477 | A1* | 2/2011 | Langer | C09K 11/06 |
| | | | | 257/40 |
| 2012/0001154 | A1* | 1/2012 | Kato | C07D 209/82 |
| | | | | 257/40 |
| 2013/0328027 | A1 | 12/2013 | Sotoyama et al. | |

FOREIGN PATENT DOCUMENTS

| | | | |
|---|---|---|---|
| JP | H08-179526 | A | 7/1996 |
| JP | 2000-086595 | A | 3/2000 |
| JP | 2012049518 | A | 3/2012 |
| KR | 10-2009-0055302 | A | 6/2009 |
| KR | 10-2011-0068239 | * | 12/2009 |
| KR | 10-2010-0028168 | A | 3/2010 |
| KR | 10-2010-0048210 | A | 5/2010 |
| KR | 10-2011-0056728 | | 5/2011 |
| KR | 10-2011-0069077 | | 5/2011 |
| KR | 10-2012-0092908 | | 8/2012 |
| KR | 10-2012-0092909 | | 8/2012 |
| KR | 2013-096647 | * | 1/2013 |
| WO | WO 2006/073059 | A1 | 7/2006 |
| WO | WO 2010/110553 | A2 | 9/2010 |
| WO | WO 2012/091471 | A2 | 7/2012 |

* cited by examiner

AMINE DERIVATIVE, AND ORGANIC ELECTROLUMINESCENCE MATERIAL AND ORGANIC ELECTROLUMINESCENCE DEVICE USING THE SAME

CROSS-REFERENCE TO RELATED APPLICATION

Japanese Patent Application No. 2012-266773, filed on Dec. 5, 2012, in the Korean Intellectual Property Office, and entitled: "Amine Derivative, and Organic Electroluminescence Material and Organic Electroluminescence Device using the Same," is incorporated by reference herein in its entirety.

BACKGROUND

1. Field

Embodiments relate to an amine derivative, and organic electroluminescence material and organic electroluminescence device using the same.

2. Description of the Related Art

In recent years, organic electroluminescence displays (organic EL displays) in which a light-emitting material is used in a light-emitting device of a display part have been actively developed. Unlike a liquid crystal display and the like, the organic EL display is a so-called self-luminescent display, which recombines holes and electrons injected from a positive electrode and a negative electrode in an emission layer to thus emit a light from a light-emitting material including an organic compound of the emission layer, thereby performing display.

SUMMARY

Embodiments are directed to an amine derivative represented by compound (I) of following Formula 1:

[Formula 1]

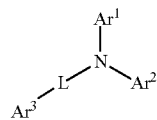

(1)

In the above Formula 1, each of $Ar^1$, $Ar^2$, and $Ar^3$ may independently represent a substituted or unsubstituted aryl group, or a substituted or unsubstituted heteroaryl group, and at least one of $Ar^1$, $Ar^2$, and $Ar^3$ may be substituted with a substituted or unsubstituted silyl group, and L may be a linker, a substituted or unsubstituted arylene group, or a substituted or unsubstituted heteroarylene group.

At least one of $Ar^1$, $Ar^2$, and $Ar^3$ may be the substituted or unsubstituted heteroaryl group.

Each of $Ar^1$ and $Ar^2$ may independently be the substituted or unsubstituted aryl group.

Each of $Ar^1$ and $Ar^2$ may independently be an aryl group having 6 to 18 carbon atoms, and $Ar^3$ may be a substituted or unsubstituted dibenzohetero group.

The silyl group substituted into at least one of $Ar^1$, $Ar^2$, and $Ar^3$ may be a triarylsilyl group of 18 to 30 carbon atoms or a trialkylsilyl group of 3 to 18 carbon atoms.

Each of $Ar^1$ and $Ar^2$ may be substituted with a silyl group.

Each of $Ar^1$, $Ar^2$, and $Ar^3$ may be substituted with a silyl group.

L may be a linker or an arylene group having 6 to 14 carbon atoms.

Embodiments also relate to a material for an organic electroluminescence device, the material including the amine derivative according to an embodiment.

Embodiments also relate to a hole transport material for an organic electroluminescence device, the hole transport material including the amine derivative according to an embodiment.

Embodiments also relate to an organic electroluminescence device including at least an emission layer and a hole transport layer disposed between a negative electrode and a positive electrode, the hole transport layer including the amine derivative according to an embodiment.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
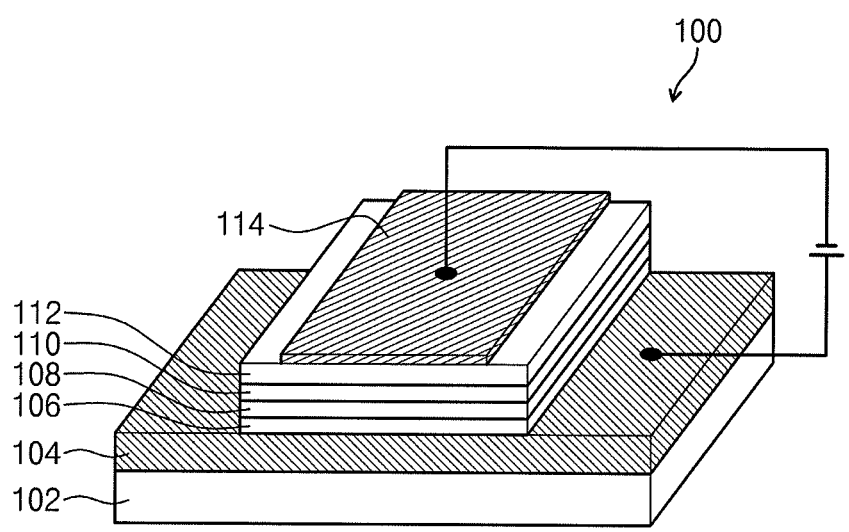
FIG. 1 is a schematic cross-sectional view illustrating the structure of an organic EL device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. In the drawing figures, the dimensions of layers and regions may be exaggerated for clarity of illustration. Like reference numerals refer to like elements throughout.

An example embodiment relates to an amine derivative having a silyl group, which may be used as a material of a hole transport layer in an organic EL device. The material may provide an organic EL device with a long life.

Hereinafter, an amine derivative having a silyl group according to an example embodiment will be explained.

The organic EL material according to the present example embodiment is an amine derivative having a silyl group represented by compound (I) of the following Formula 2.

[Formula 2]

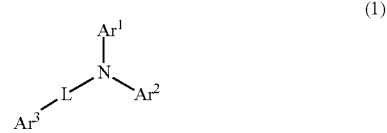

(1)

According to the present example embodiment, each of $Ar^1$, $Ar^2$, and $Ar^3$ independently represents a substituted or unsubstituted aryl group, or a substituted or unsubstituted heteroaryl group, at least one of $Ar^1$, $Ar^2$, and $Ar^3$ is substituted with a substituted or unsubstituted silyl group. L is a linker, a substituted or unsubstituted arylene group, or a substituted or unsubstituted heteroarylene group.

The aryl group and the heteroaryl group in the "substituted or unsubstituted aryl group" or the "substituted or unsubstituted heteroaryl group" of $Ar^1$, $Ar^2$, and $Ar^3$ may include, for example, a phenyl group, a naphthyl group, an anthracenyl group, a phenanthryl group, a biphenyl group, a terphenyl group, a fluorenyl group, a triphenylene group, a biphenylene group, a pyrenyl group, a benzothiazolyl group, a thiophenyl group, a thienothiophenyl group, a thienothienothiophenyl group, a benzothiophenyl group, a dibenzothiophenyl group, a dibenzofuryl group, an N-arylcarbazolyl group, an N-heteroarylcarbazolyl group, an N-alkylcarbazolyl group, a phenoxazinyl group, a phenothiazinyl group, a pyridyl group, a pyrimidyl group, a triazile group, a quinolinyl group, or a quinoxaline group. In an implementation, the aryl group or the heteroaryl group of $Ar^1$, $Ar^2$, and $Ar^3$ includes, for example, the phenyl group, the naphthyl group, the biphenyl group, the terphenyl group, the fluorenyl group, the triphenylene group, the dibenzothiophenyl group, the dibenzofuryl group, or the N-phenylcarbazolyl group. In an implementation, the aryl group or the heteroaryl group of $Ar^1$, $Ar^2$, and $Ar^3$ includes the phenyl group, the biphenyl group, the fluorenyl group, the triphenylene group, the dibenzothiophenyl group, the dibenzofuryl group, or the N-phenylcarbazolyl group.

According to the present example embodiment, at least one of the aryl group or the heteroaryl group of $Ar^1$, $Ar^2$, and $Ar^3$ is substituted with the silyl group. In addition, in an example embodiment, at least one of $Ar^1$ and $Ar^2$ may be substituted with silyl groups each independently. In another example embodiment, at least one of $Ar^1$, $Ar^2$, and $Ar^3$ may be substituted with silyl groups each independently.

In an example embodiment, at least one of $Ar^1$, $Ar^2$, and $Ar^3$ may be the substituted or unsubstituted heteroaryl group, and in another example embodiment, $Ar^1$, $Ar^2$, and $Ar^3$ may be a substituted or unsubstituted fluorenyl group or a dibenzohetero group such as a carbazolyl group, a dibenzothiophenyl group, a dibenzofuryl group, etc. In addition, in an example embodiment, $Ar^3$ may be the substituted or unsubstituted heteroaryl group, and in another example embodiment, $Ar^3$ may be a dibenzohetero group. When $Ar^3$ is the substituted or unsubstituted heteroaryl group, $Ar^1$ and $Ar^2$ may be the substituted or unsubstituted aryl group. In an example embodiment, $Ar^3$ may be a dibenzohetero group, and $Ar^1$ and $Ar^2$ may be an aryl group having 6 to 18 carbon atoms.

The "substituted or unsubstituted arylene group" and the "substituted or unsubstituted heteroarylene group" of L may include, for example, the same aryl group and the heteroaryl group of the "substituted or unsubstituted aryl group" or the "substituted or unsubstituted heteroaryl group" of $Ar^1$, $Ar^2$, and $Ar^3$. The arylene group and the heteroarylene group of the "substituted or unsubstituted arylene group" and the "substituted or unsubstituted heteroarylene group" of L may include, for example, a phenylene group, a naphthalene group, a biphenylylene group, a thienothiophenylene group, or a pyridylene group. In an example embodiment, an arylene group having 6 to 14 carbon atoms may be used, and the phenylene group and the biphenylylene group may be used. In addition, when L is referred to as the "linker," a nitrogen atom (N) around an amine is directly connected to $Ar^3$ in the amine derivative having a silyl group. For example, L is the "linker," i.e., a nitrogen atom (N) around an amine is directly connected by a bond to $Ar^3$ in the amine derivative having a silyl group, in compound 1.

Substituents for the aryl group or the heteroaryl group of $Ar^1$, $Ar^2$, and $Ar^3$ may include, for example, an alkyl group, an alkoxy group, an aryl group, or a heteroaryl group. Particular examples of the aryl group and the heteroaryl group may be the same as those of $Ar^1$, $Ar^2$, and $Ar^3$.

The alkyl group as the substituent for the aryl group or the heteroaryl group of $Ar^1$, $Ar^2$, and $Ar^3$ may include, for example, a methyl group, an ethyl group, a propyl group, an isopropyl group, a cyclopropyl group, a butyl group, an isobutyl group, a tert-butyl group, a cyclobutyl group, a pentyl group, an isopentyl group, a neopentyl group, a cyclopentyl group, a hexyl group, a cyclohexyl group, an heptyl group, a cycloheptyl group, an octyl group, a nonyl group, a decyl group, or the like.

The alkoxy group as the substituent for the aryl group or the heteroaryl group of $Ar^1$, $Ar^2$, and $Ar^3$ may include, for example, a methoxy group, an ethoxy group, an n-propoxy group, an isopropoxy group, an n-butoxy group, an isobutoxy group, a tert-butoxy group, an n-pentyloxy group, a neopentyl group, an n-hexyloxy group, an n-heptyloxy group, an n-octyloxy group, a 2-ethylhexyloxy group, a nonyloxy group, a decyloxy group, a 3,7-dimethyloctyloxy group, or the like.

Substituents of the arylene group or the heteroarylene group of L may include, for example, an alkyl group, an alkoxy group, an aryl group, a heteroaryl group, or the like. Particular examples of the aryl group and the heteroaryl group may be the same as the alkyl group, the alkoxy group, the aryl group, and the heteroaryl group explained as the aryl group or the heteroaryl group of $Ar^1$, $Ar^2$, and $Ar^3$.

Substituents of the silyl group substituted into at least one of $Ar^1$, $Ar^2$, and $Ar^3$ may include, for example, an alkyl group, an alkoxy group, an aryl group, or a heteroaryl group. Particular examples of the aryl group and the heteroaryl group may be the same as the alkyl group, the alkoxy group, the aryl group, and the heteroaryl group explained as the substituent of the aryl group or the heteroaryl group of $Ar^1$, $Ar^2$, and $Ar^3$. In an example embodiment, the alkyl group and the aryl group may be used. For example, a methyl group and a phenyl group may be used. In addition, the silyl group substituted into at least one of $Ar^1$, $Ar^2$, and $Ar^3$ may include a trialkylsilyl group of 3 to 18 carbon atoms or a triarylsilyl group of 18 to 30 carbon atoms.

The amine derivative having a silyl group according to an example embodiment and represented by compound (I) may include, for example, the compounds represented by the following Formulae 3 to 48, however the compounds are not limited thereto.

[Formula 3]
No. 1
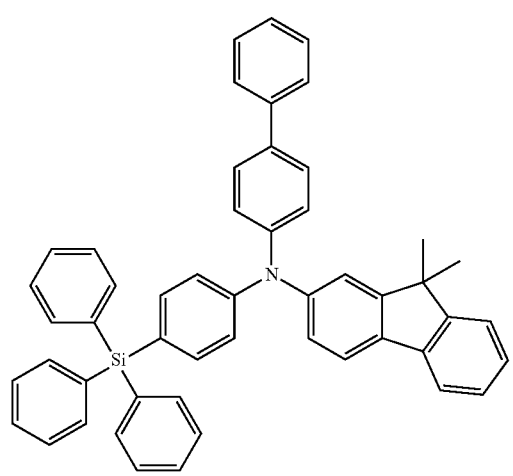
No. 2
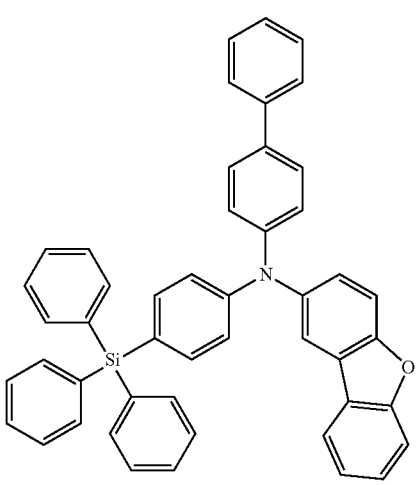
No. 3
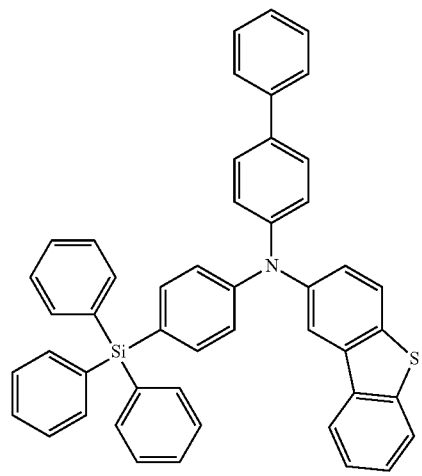
No. 4
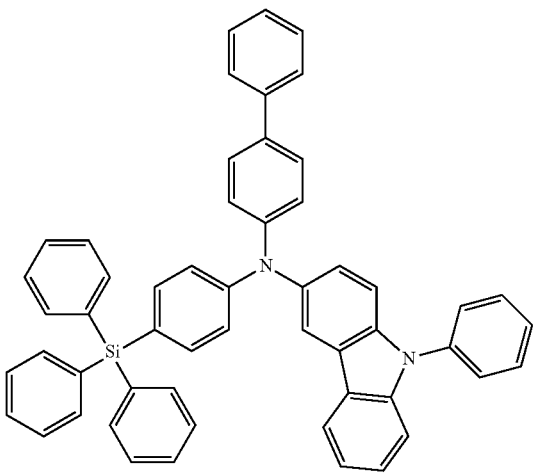
[Formula 4]
No. 5
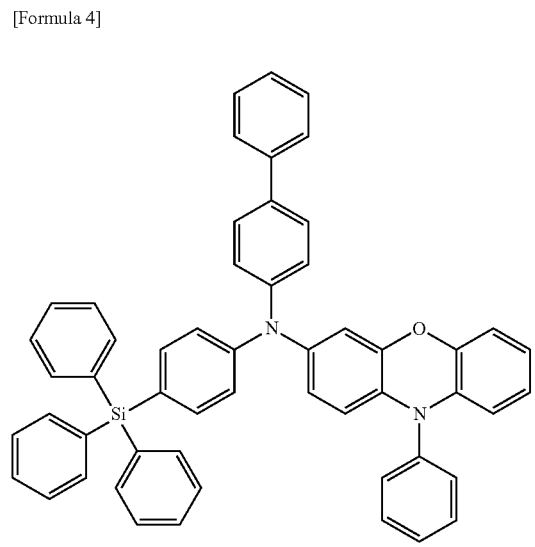
No. 6
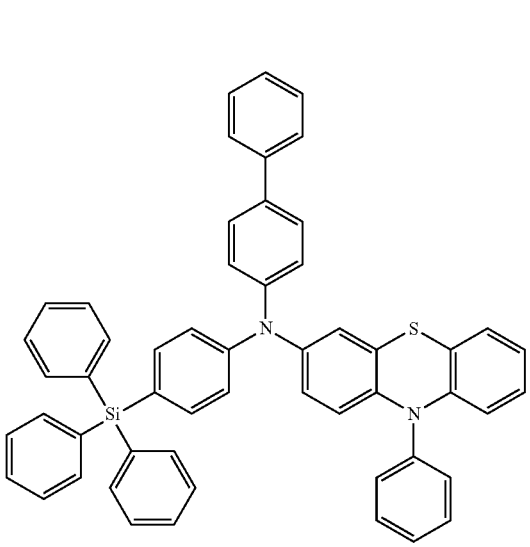

No. 7
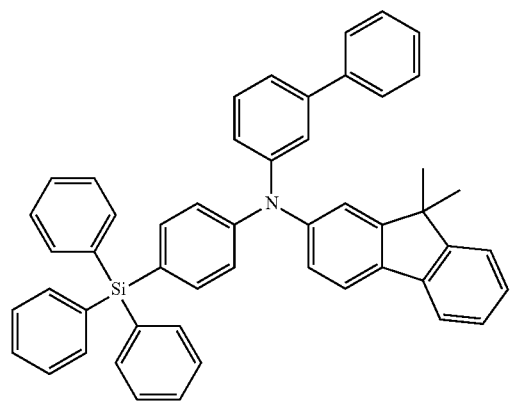
No. 8
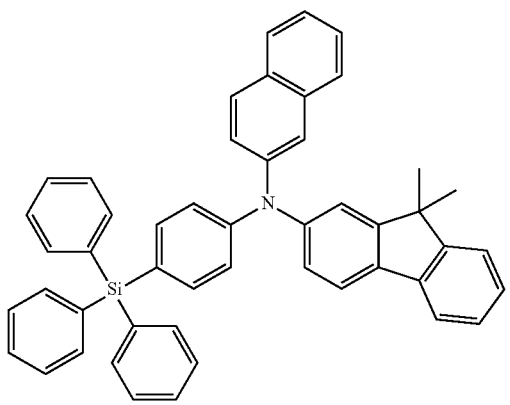
[Formula 5]
No. 9
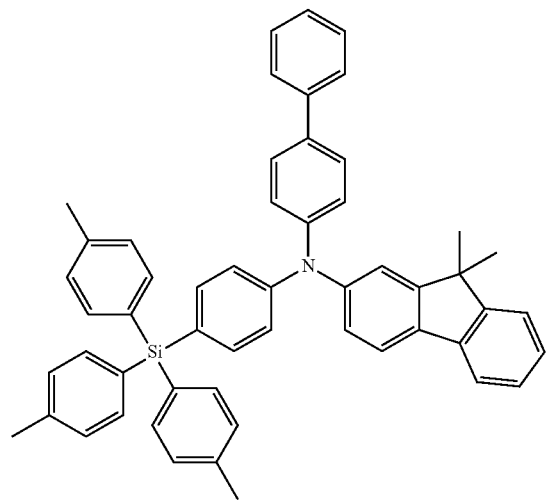
No. 10
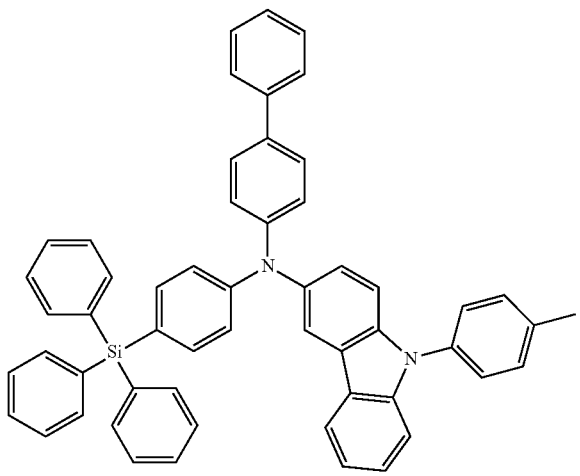
No. 11
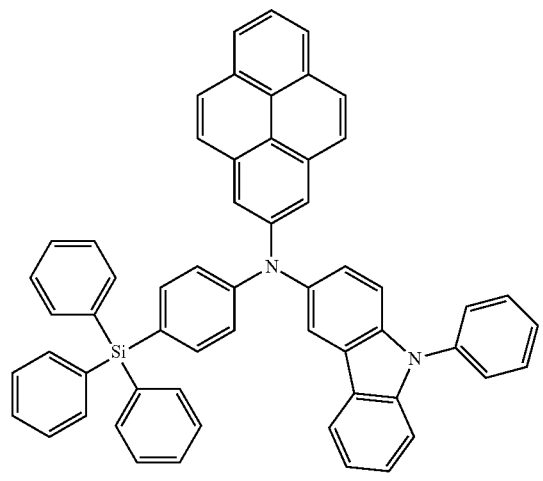
No. 12
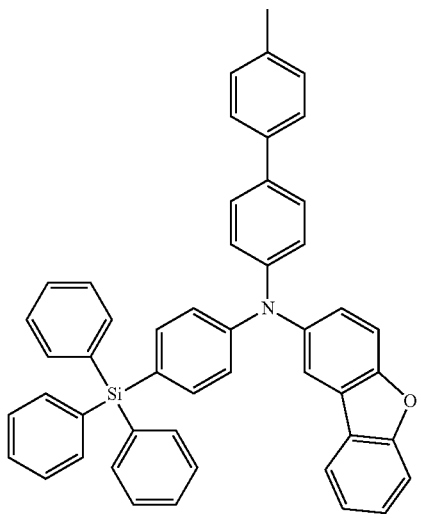

[Formula 6]
No. 13
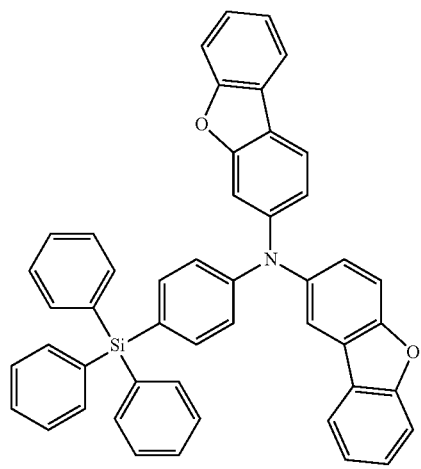
No. 14
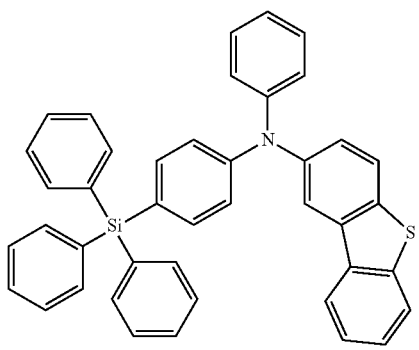
[Formula 7]
No. 15
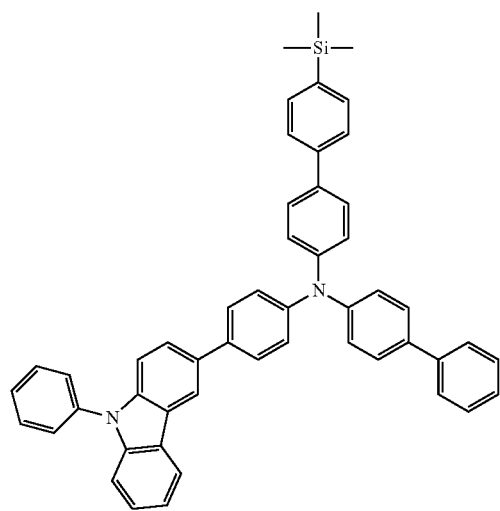
No. 16
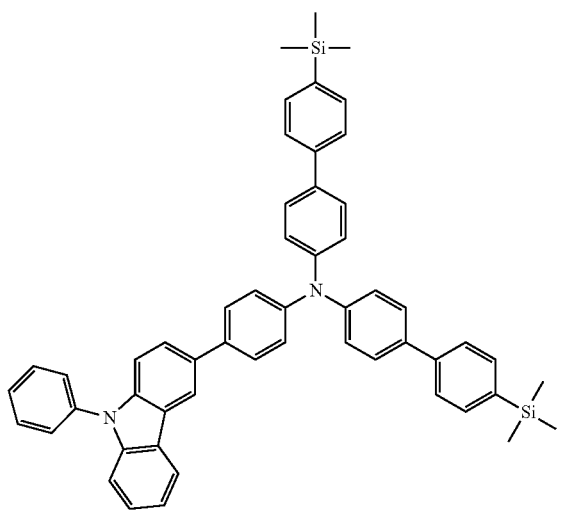
[Formula 8]
No. 17
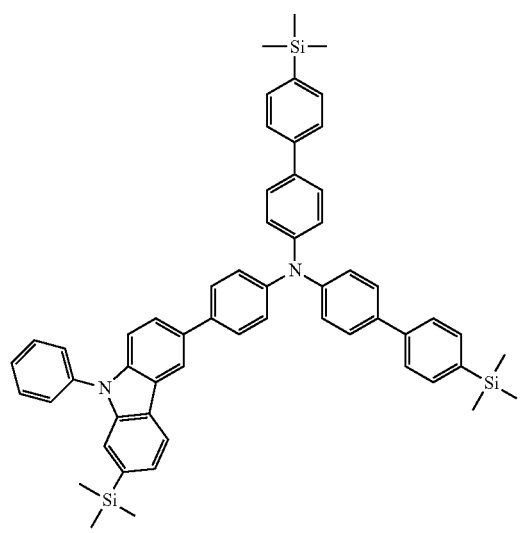
No. 18
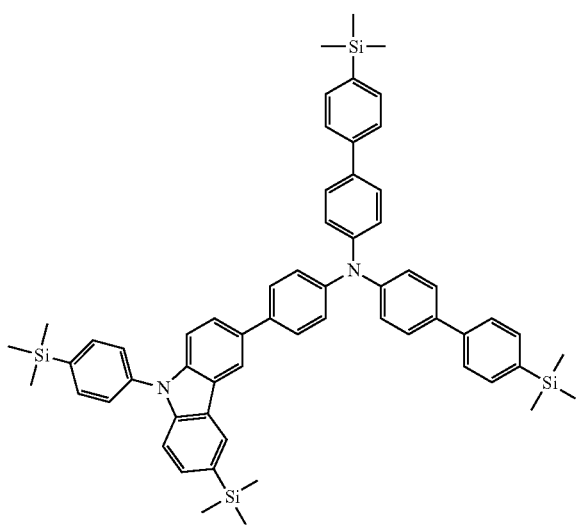

[Formula 9]
No. 19
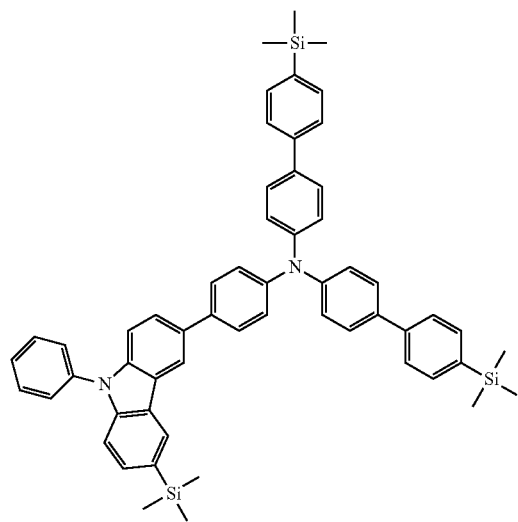
No. 20
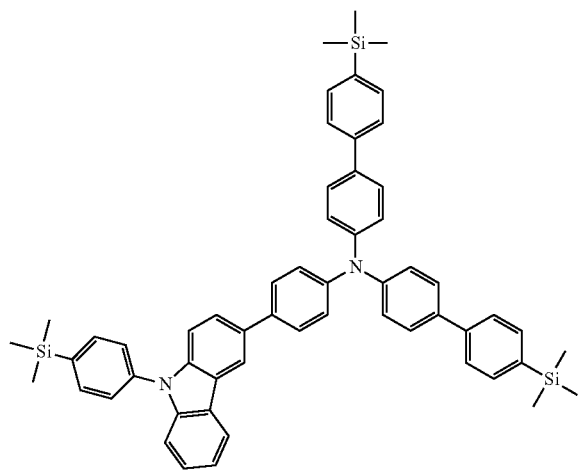
[Formula 10]
No. 21
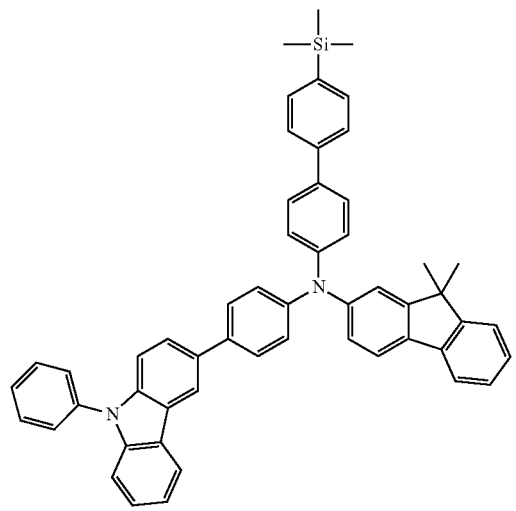
No. 22
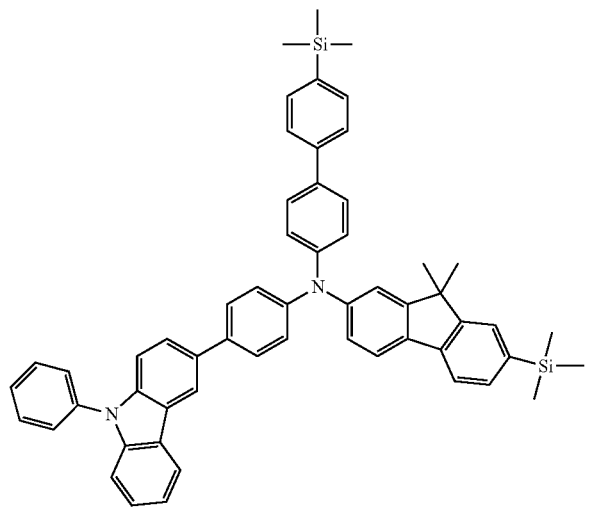

[Formula 11]
No. 23
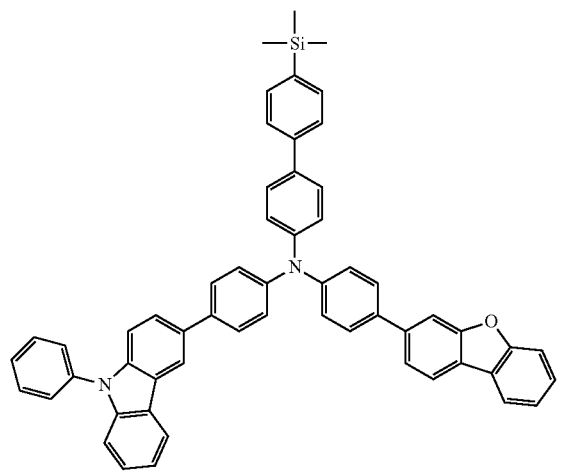
No. 24
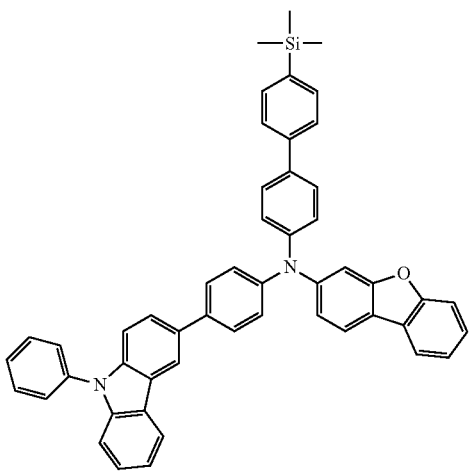
No. 25
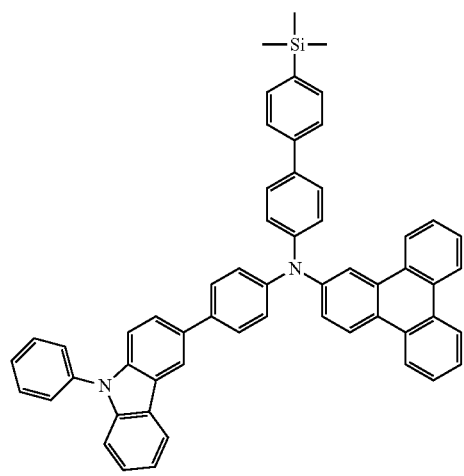
No. 26
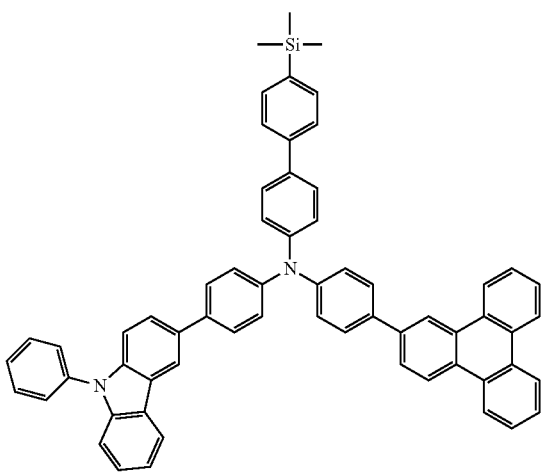

[Formula 13]
No. 27
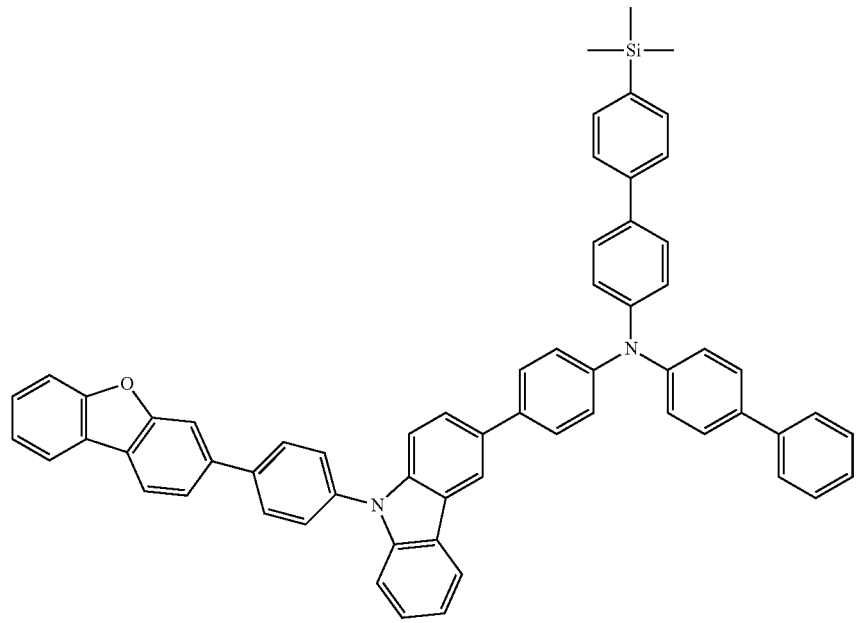
No. 28
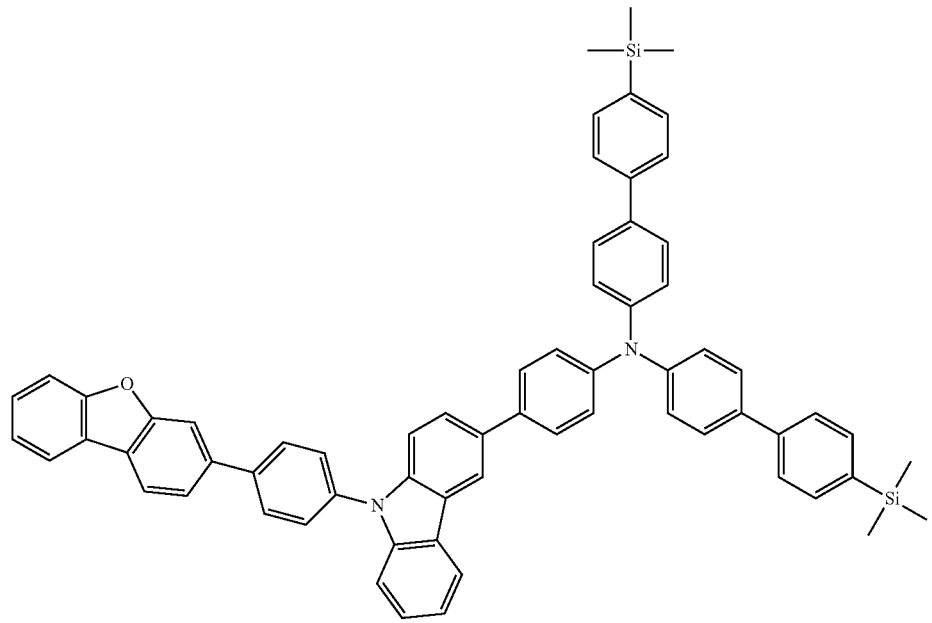

[Formula 14]
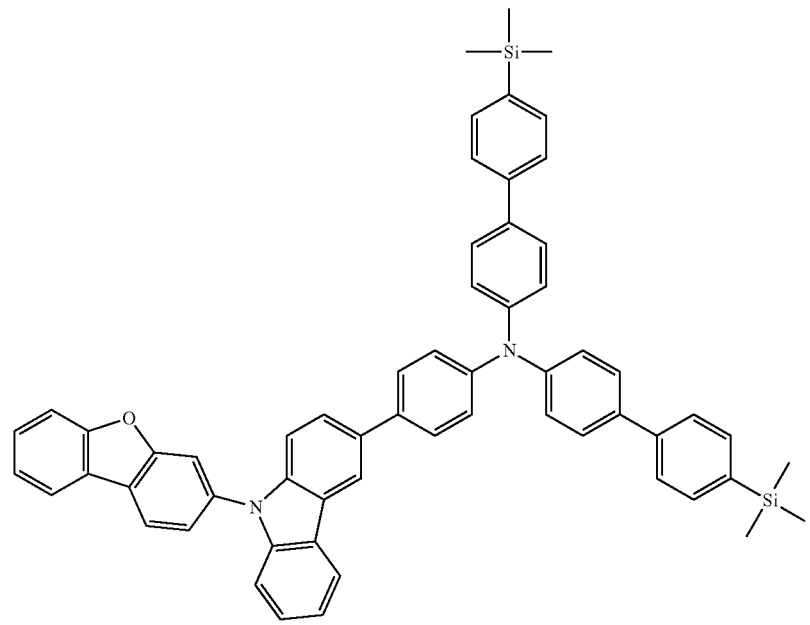
No. 29
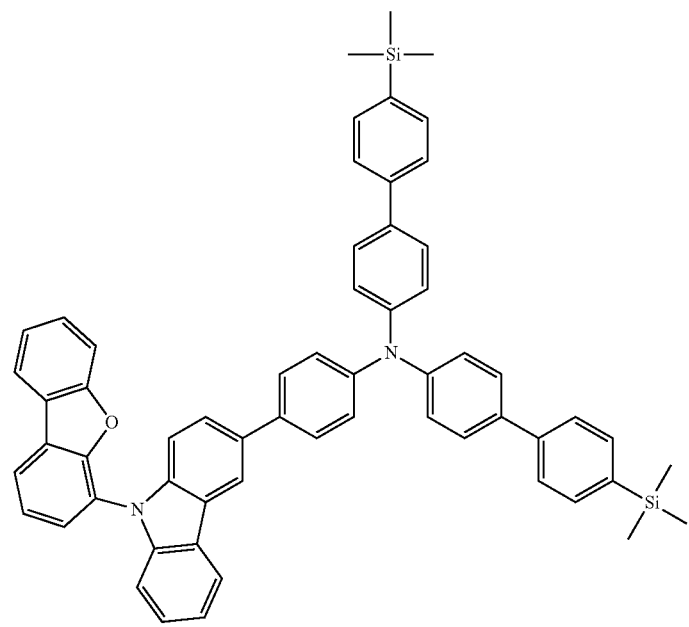
No. 30

[Formula 15]
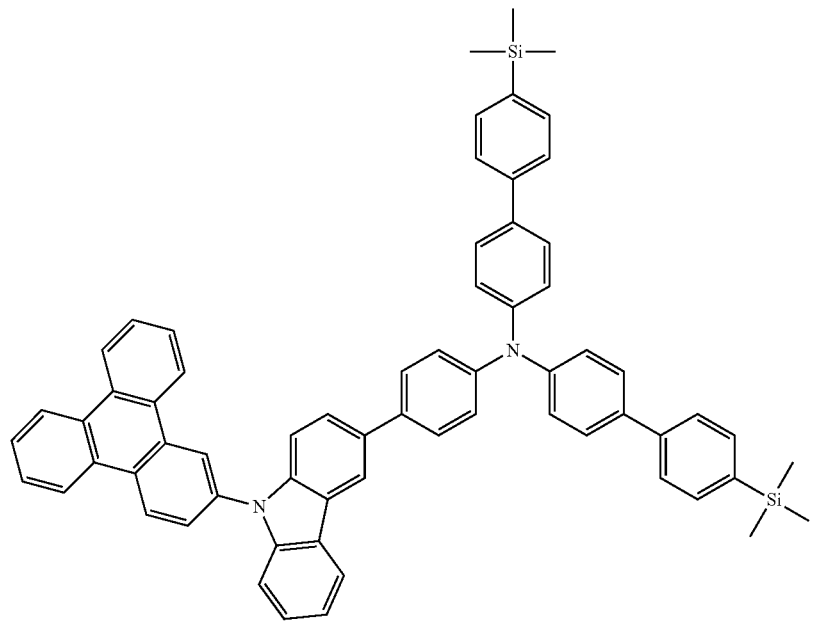
No. 31
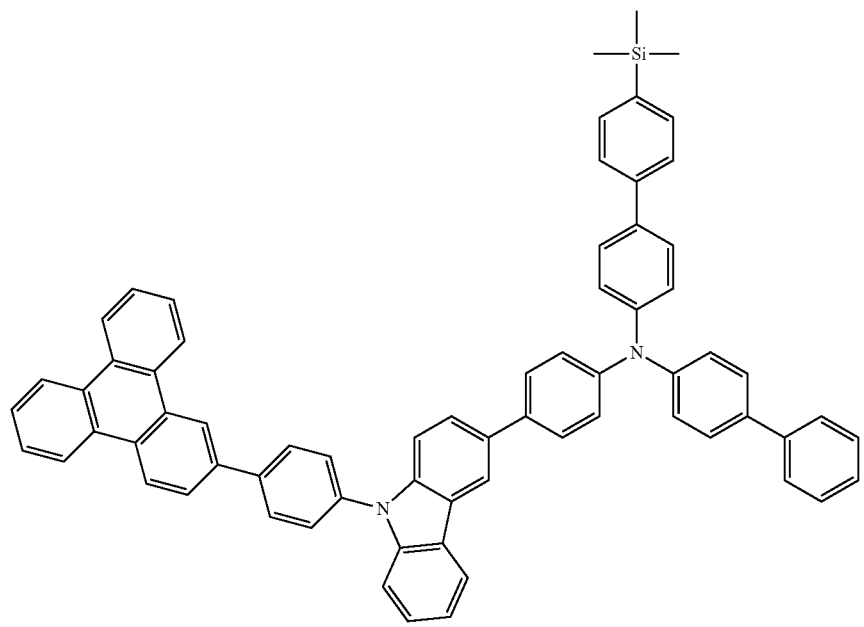
No. 32

[Formula 16]
No. 33
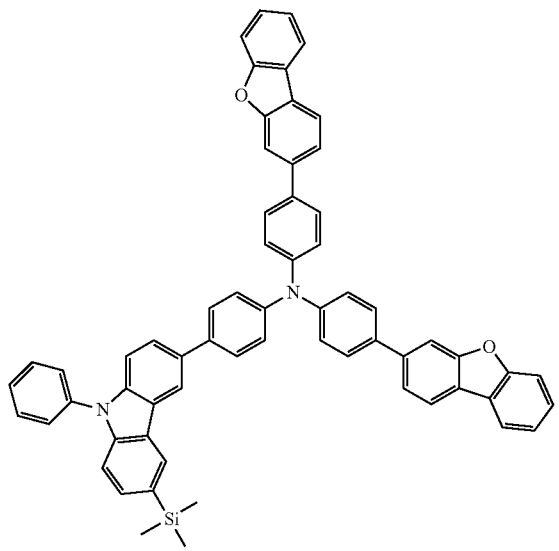
No. 34
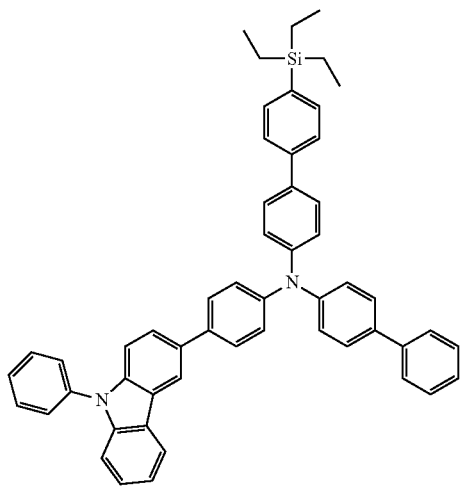
No. 35
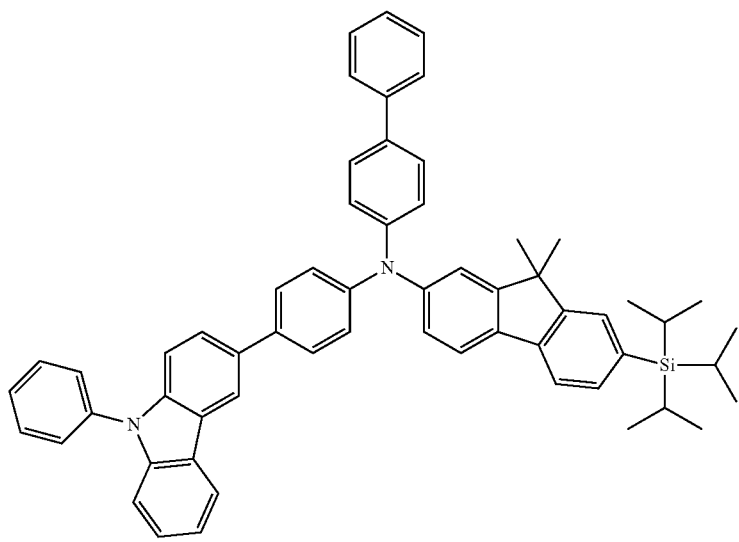

-continued
[Formula 17]
No. 36
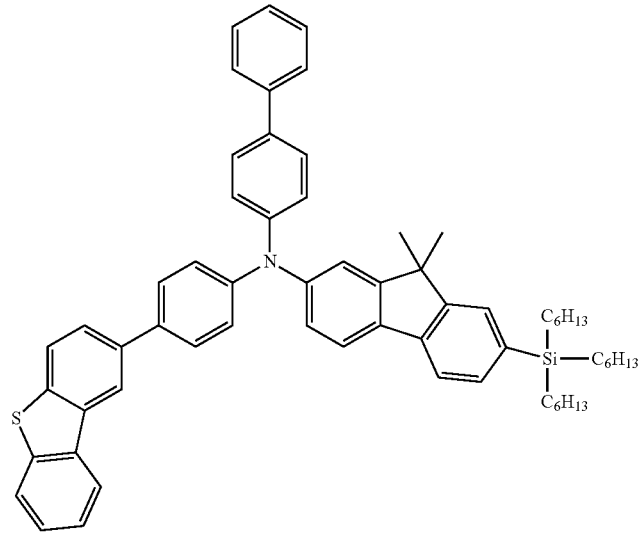
No. 37
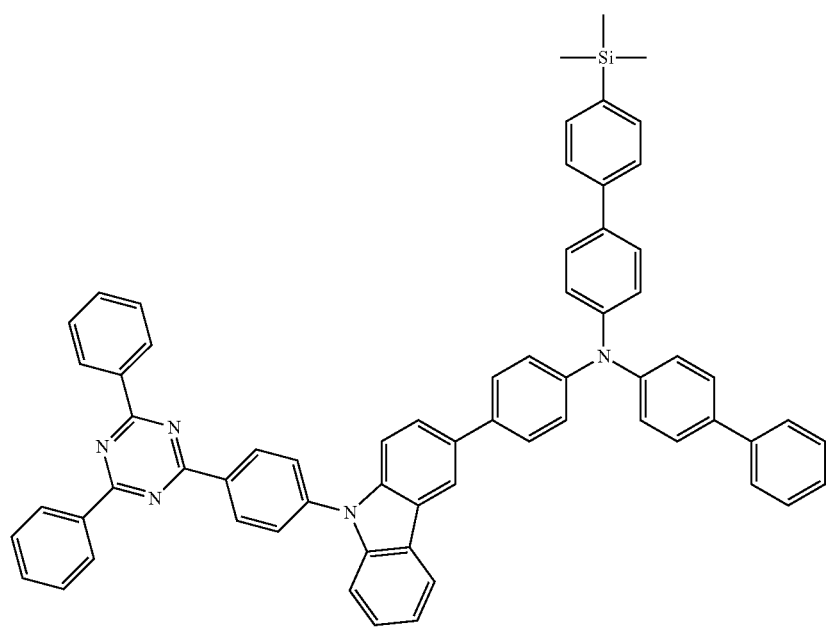

[Formula 18]
No. 38
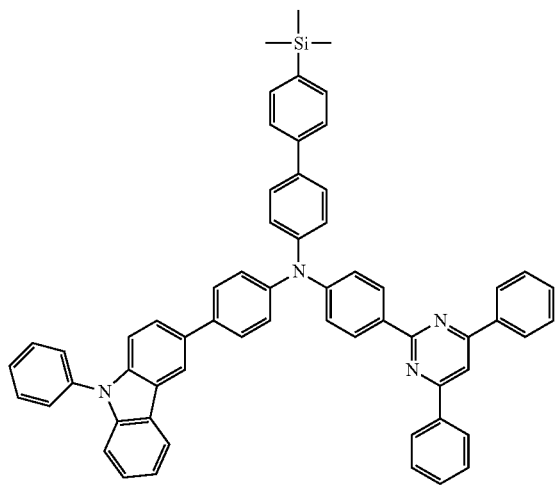
No. 39
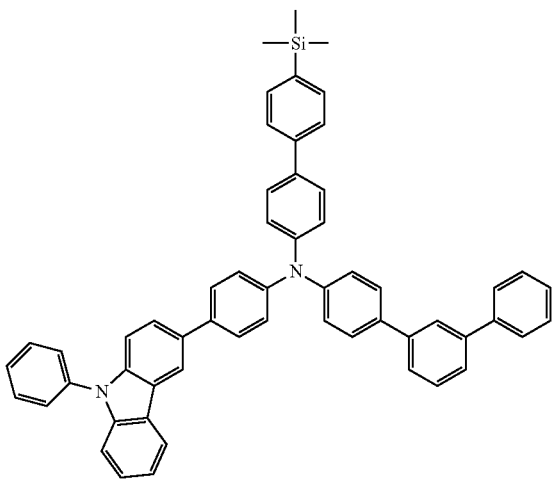
No. 40
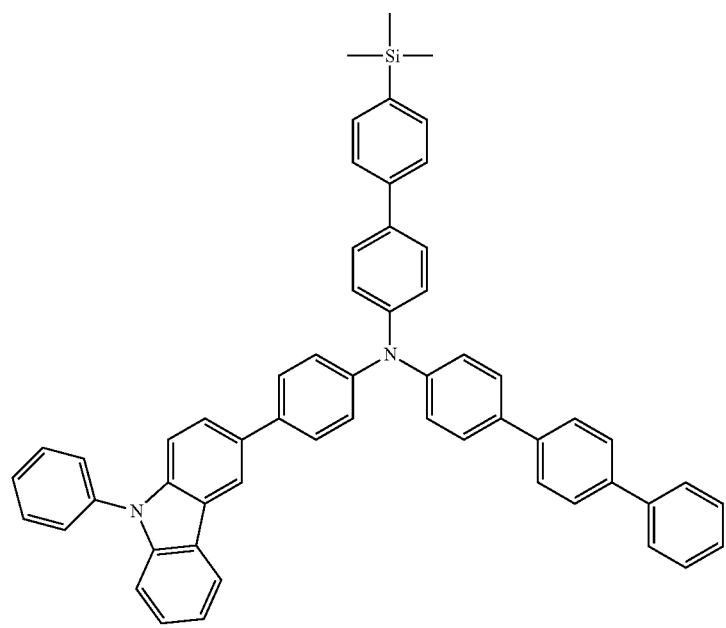

-continued
[Formula 19]
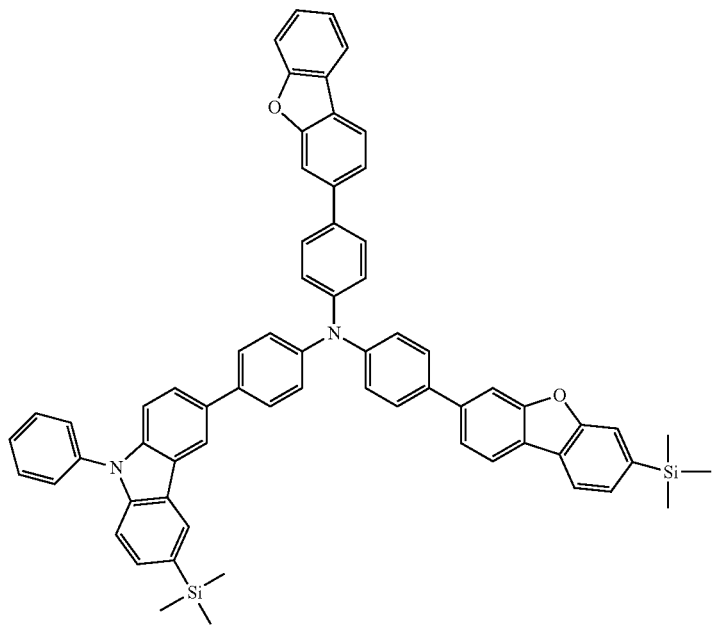
No. 41
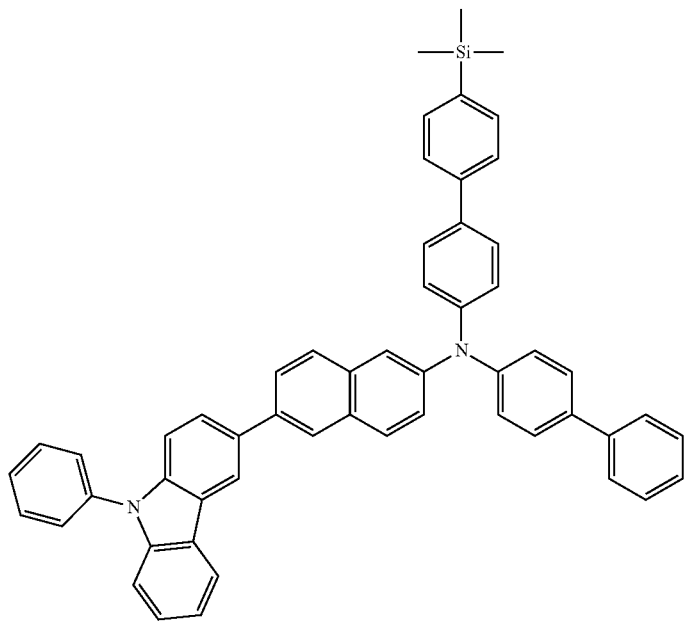
No. 42

[Formula 20]
No. 43 No. 44
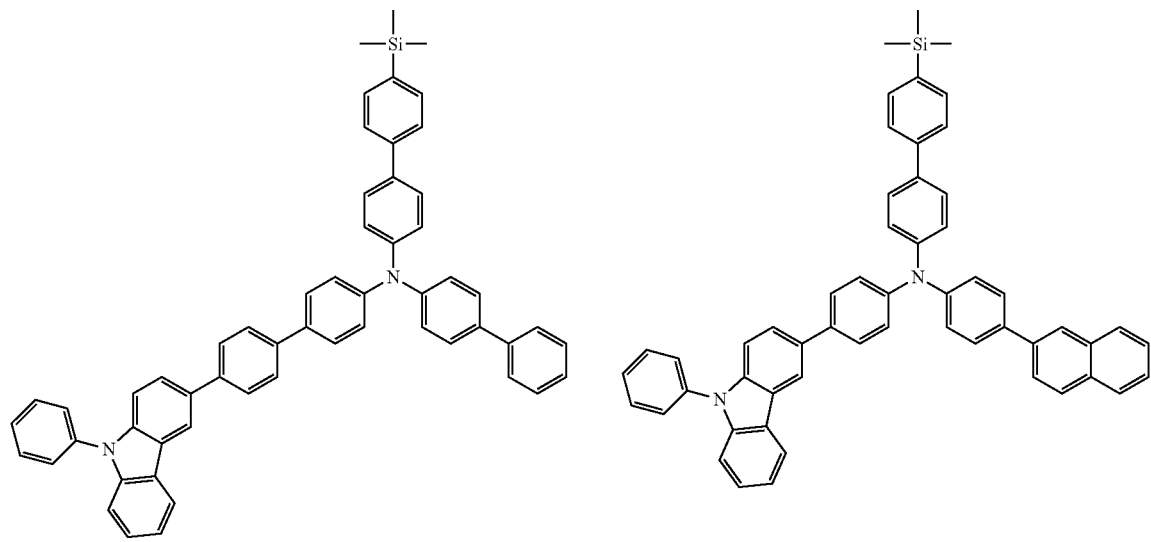
No. 45
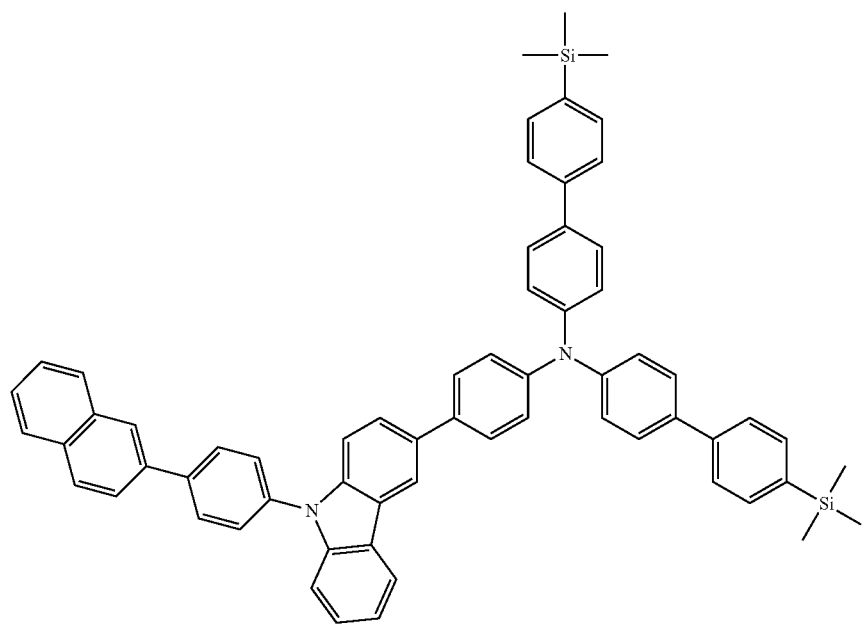

No. 46
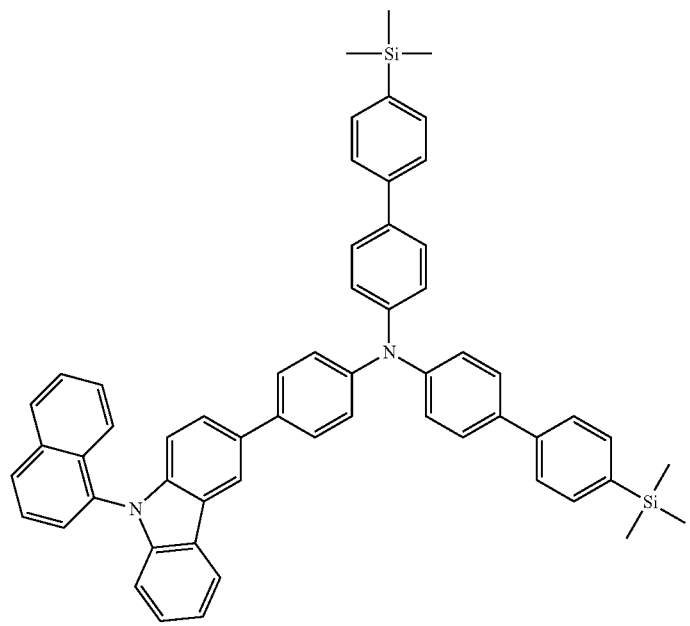
[Formula 22]
No. 47
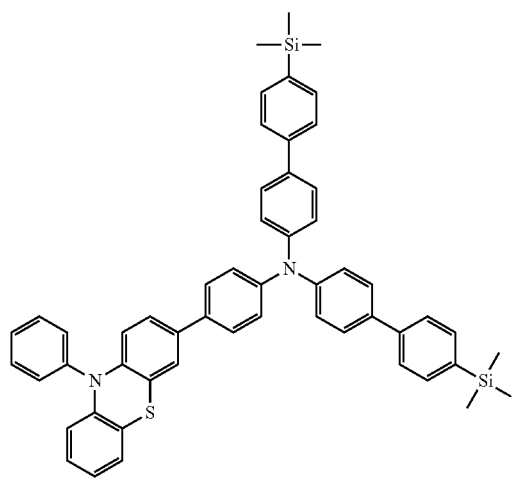
No. 48
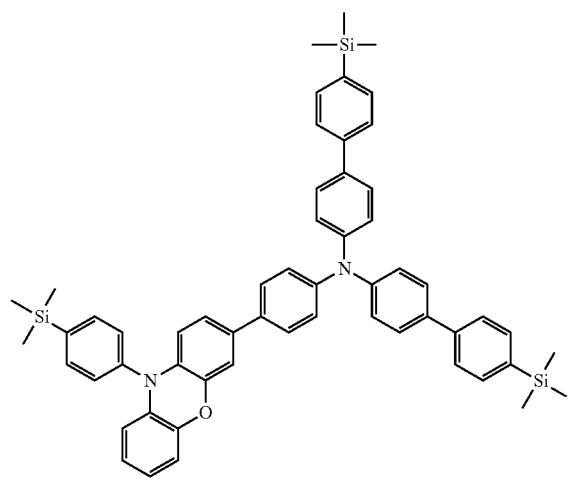

-continued
[Formula 23]
No. 49
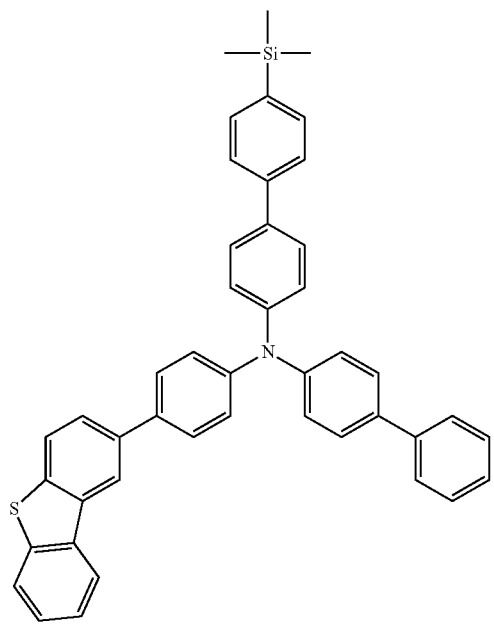
No. 50
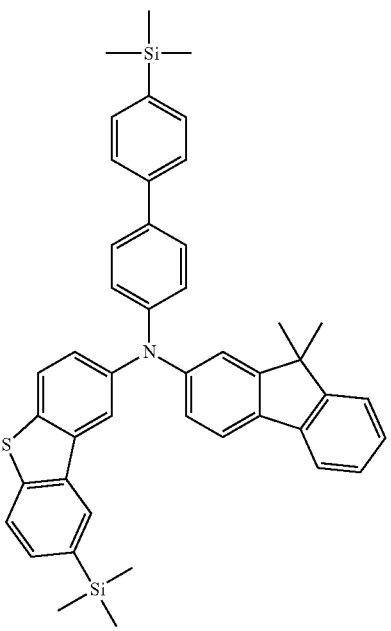
No. 51
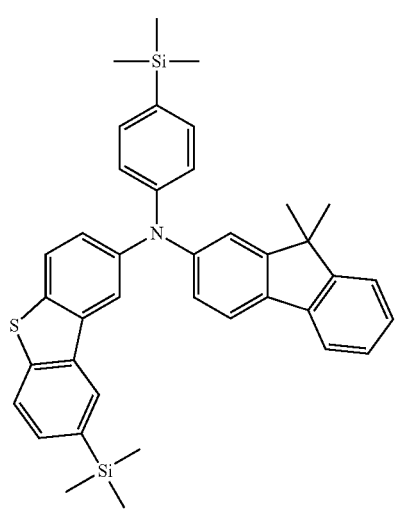

[Formula 24]
No. 52
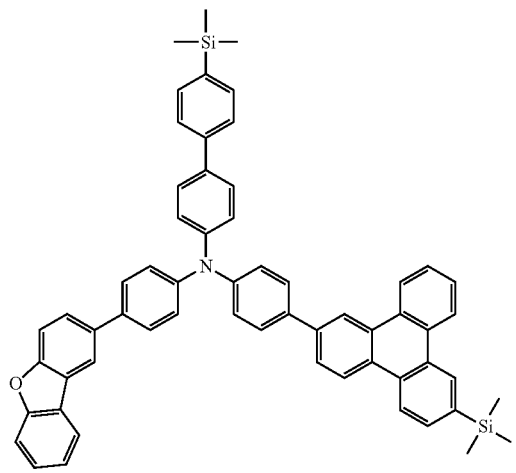
No. 53
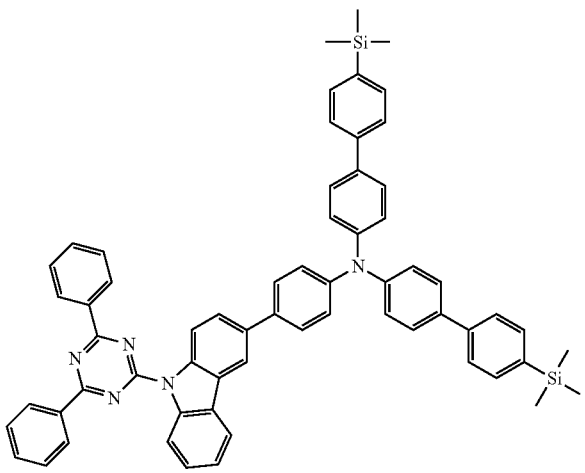
[Formula 25]
No. 54
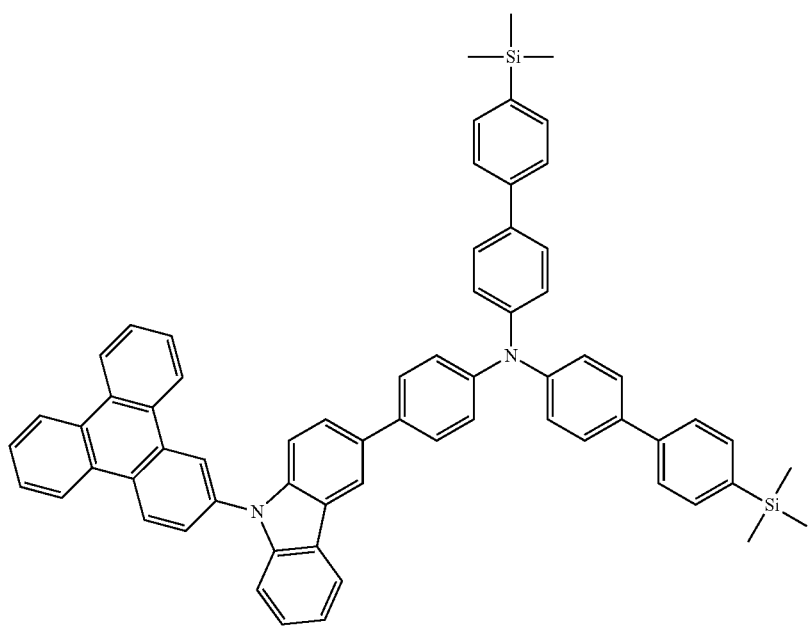

-continued
No. 55
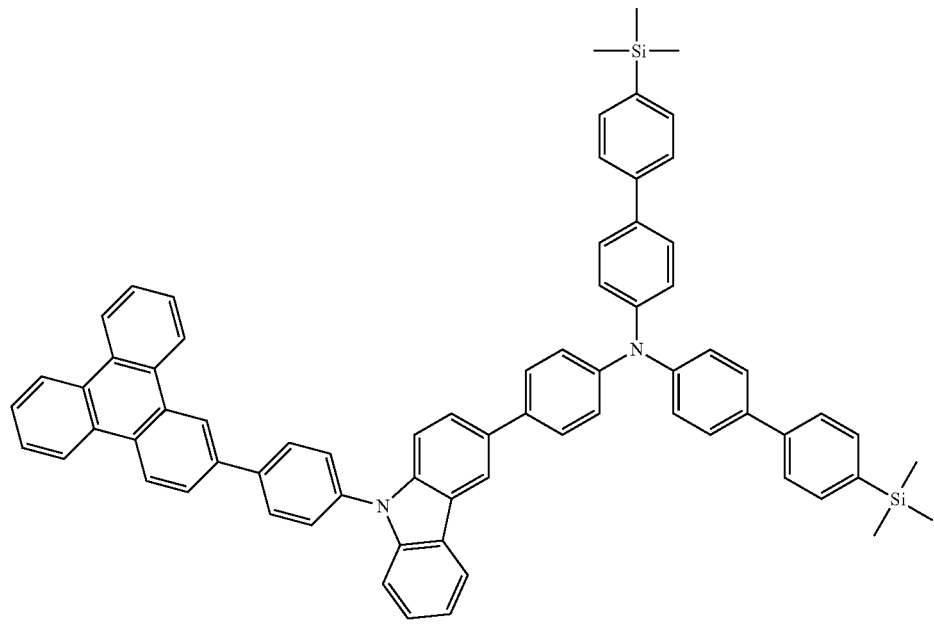
[Formula 26]
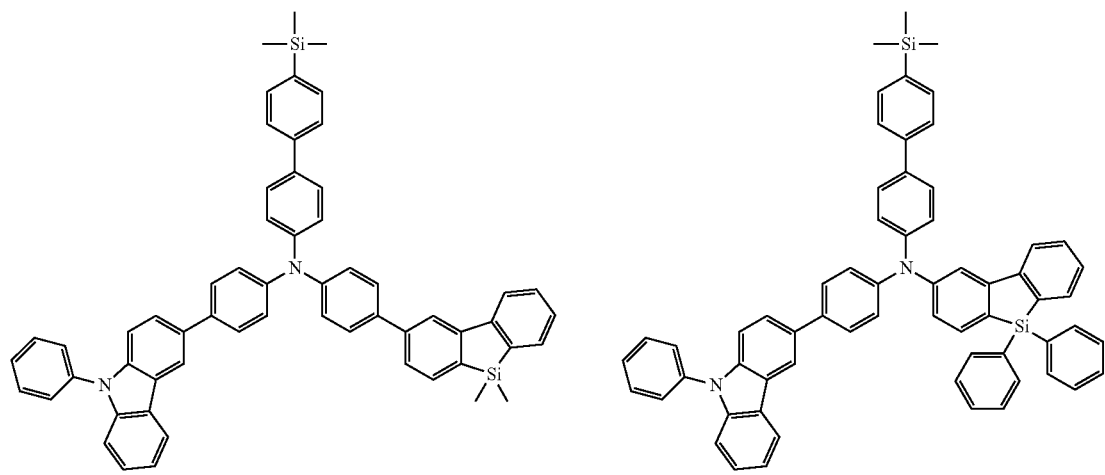
No. 56
No. 57

[Formula 27]
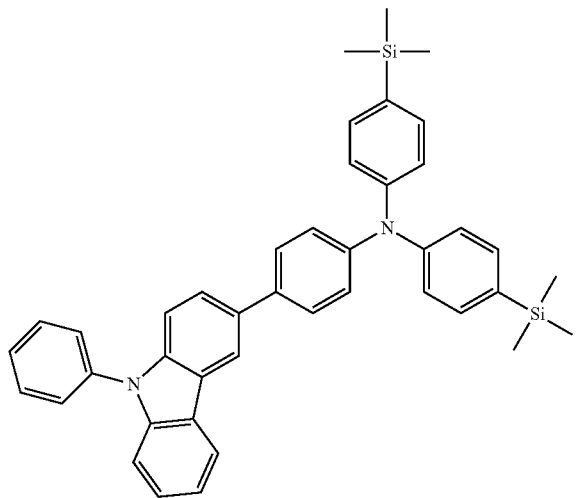
No. 58
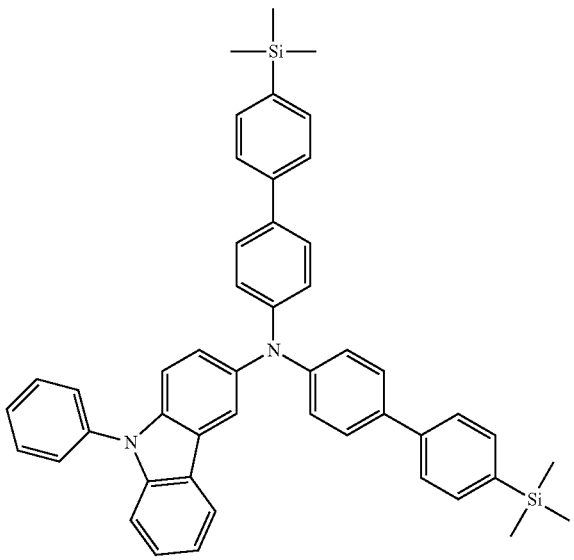
No. 59
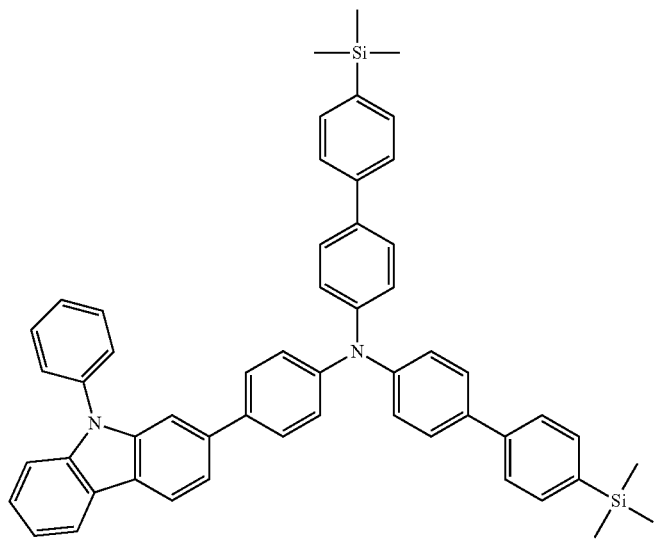
No. 60

-continued
[Formula 28]
No. 61
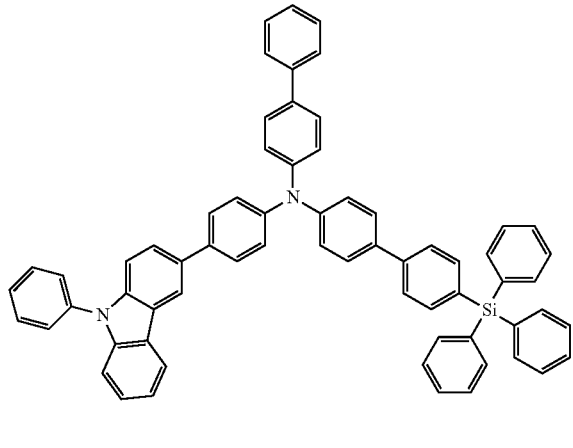
No. 62
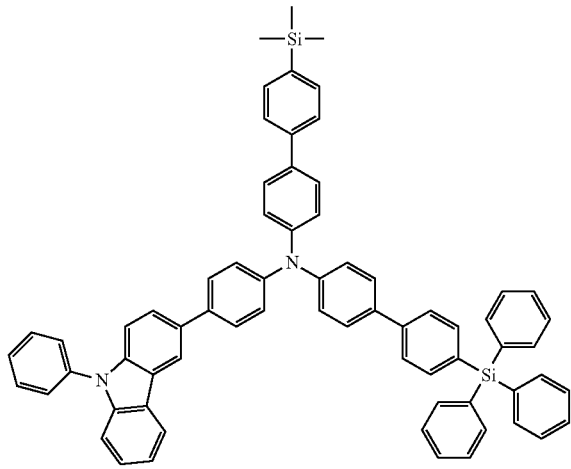
[Formula 29]
No. 63
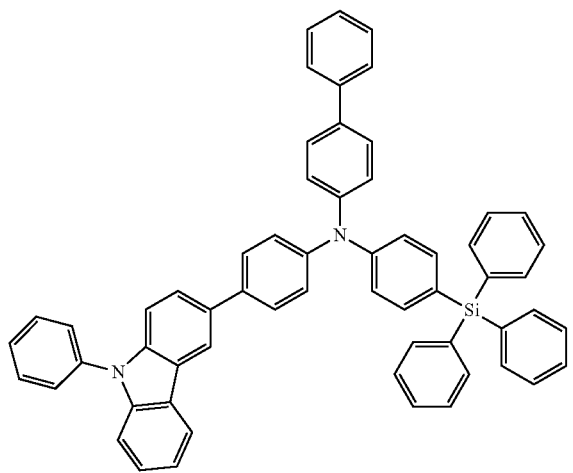
No. 64
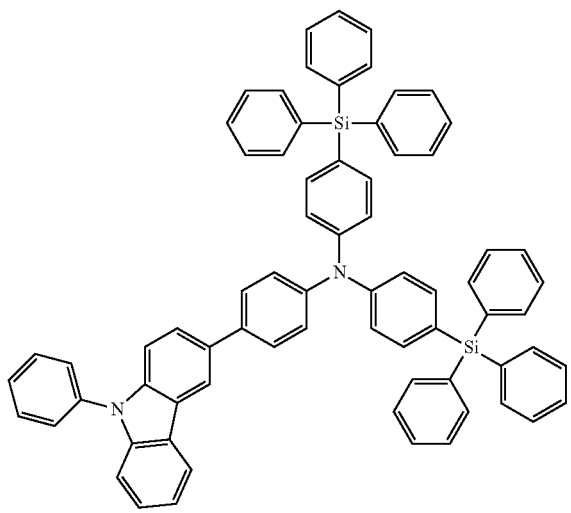
[Formula 30]
No. 65
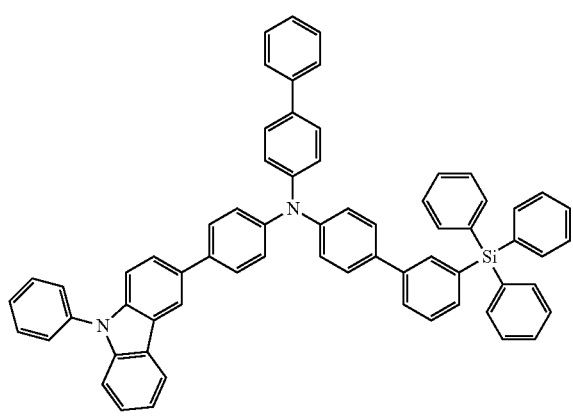
No. 66
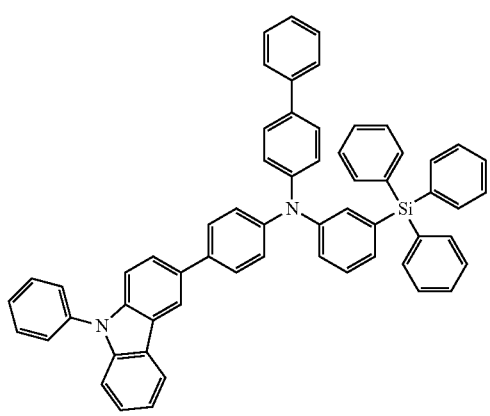

No. 67
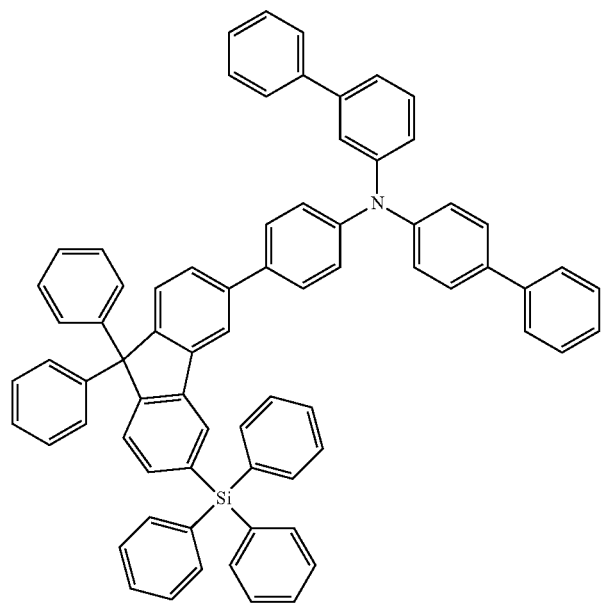
[Formula 31]
No. 68
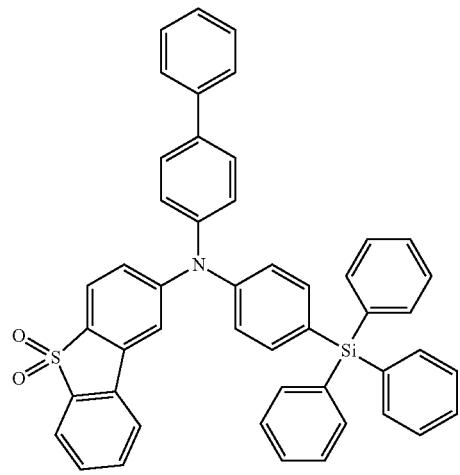
No. 69
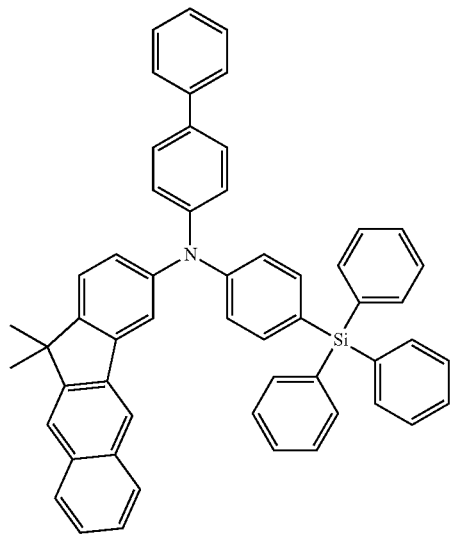

-continued
No. 70
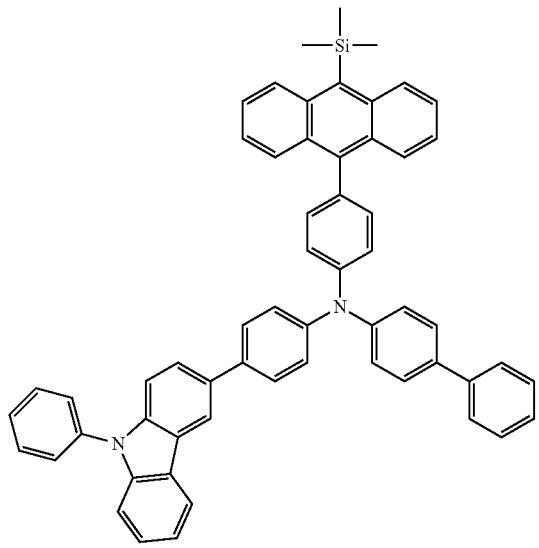
No. 71
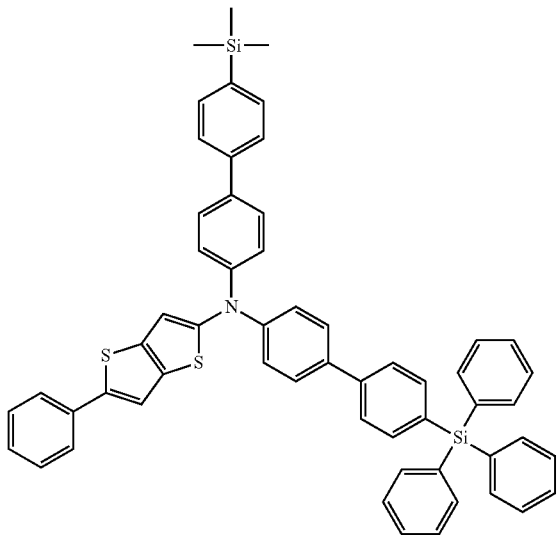
[Formula 32]
No. 72
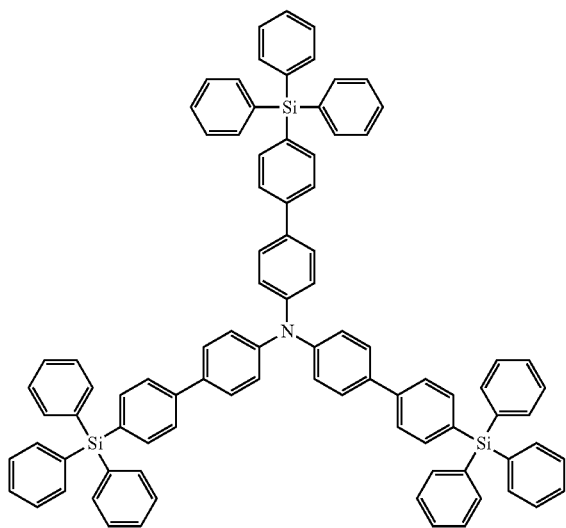
No. 73
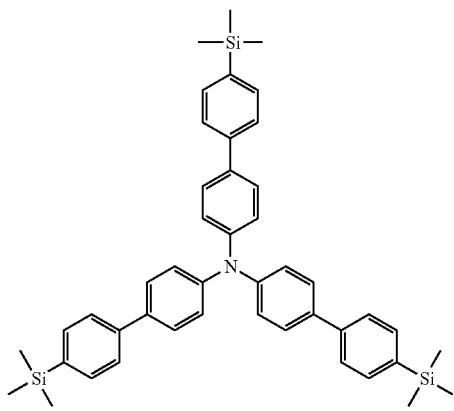

[Formula 33]
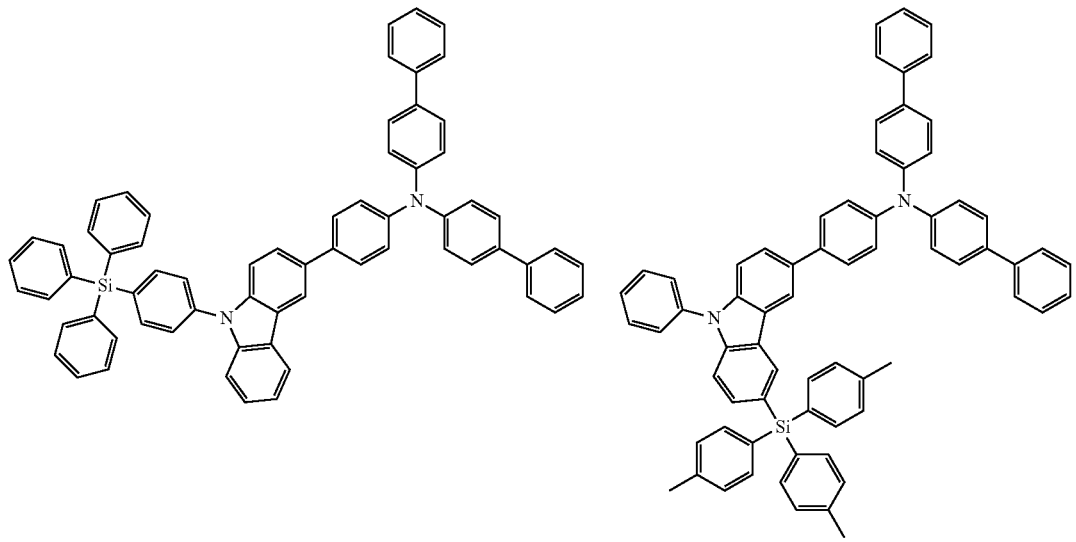
No. 74
No. 75
[Formula 34]
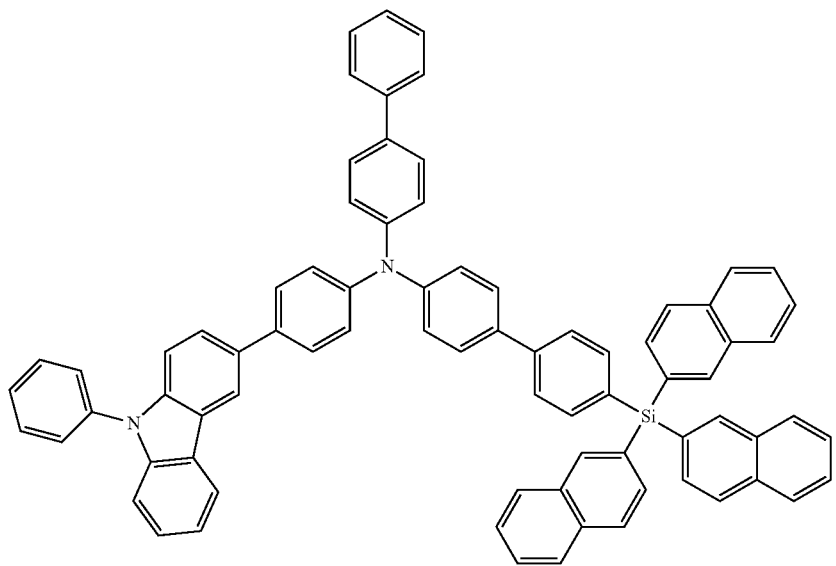
No. 76

-continued
No. 77
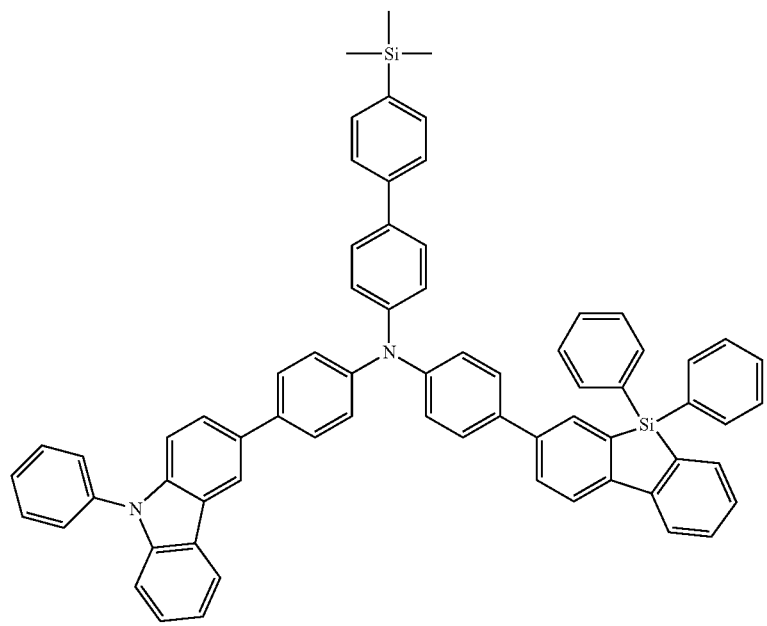
[Formula 35]
No. 78
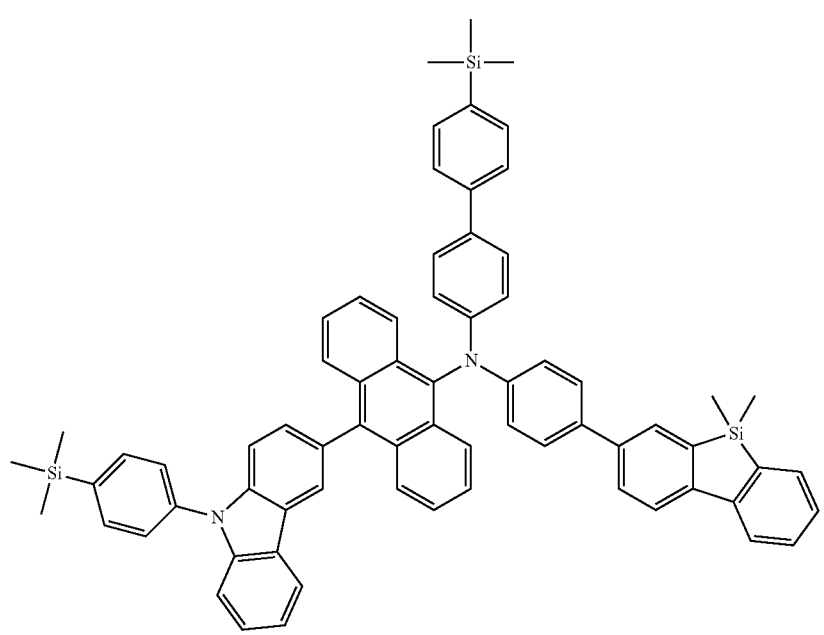

No. 79
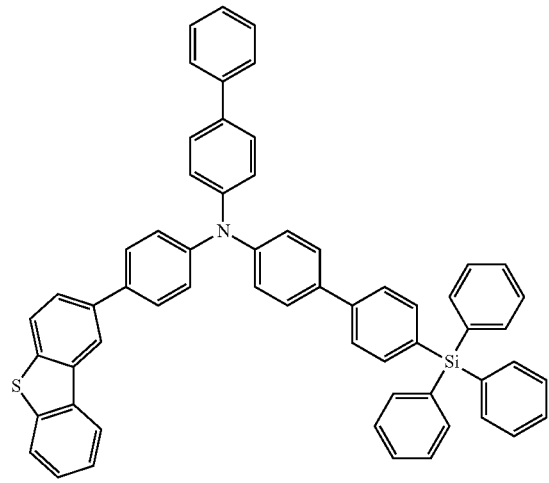
No. 80
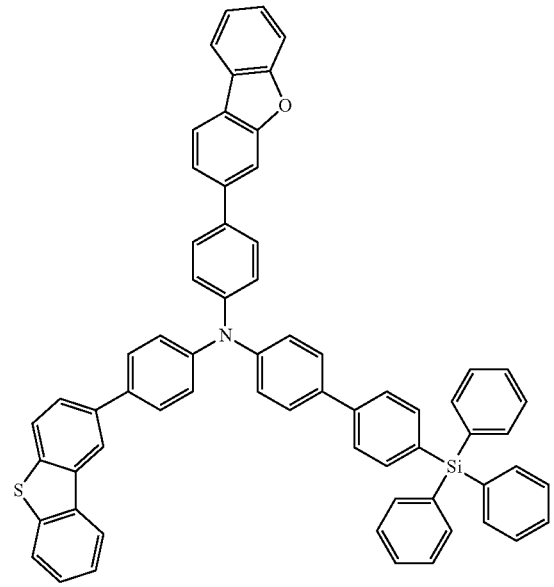
[Formula 36]
No. 81
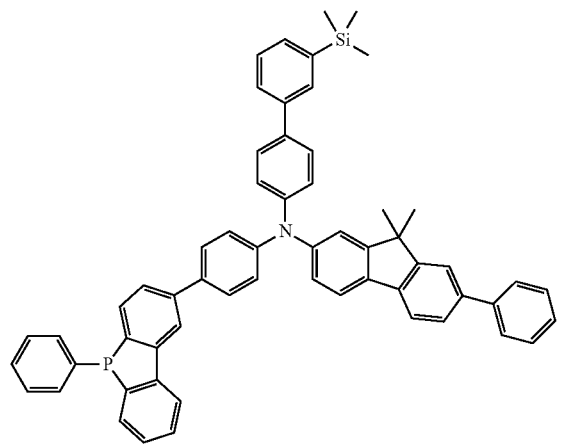
No. 82
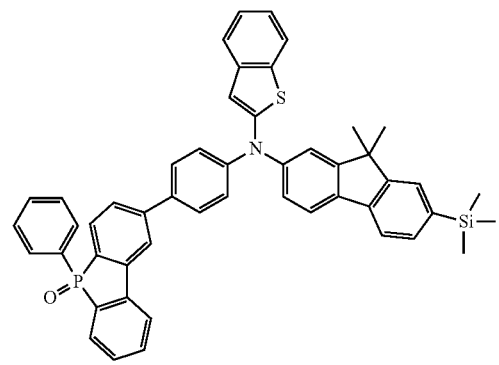
[Formula 37]
No. 83
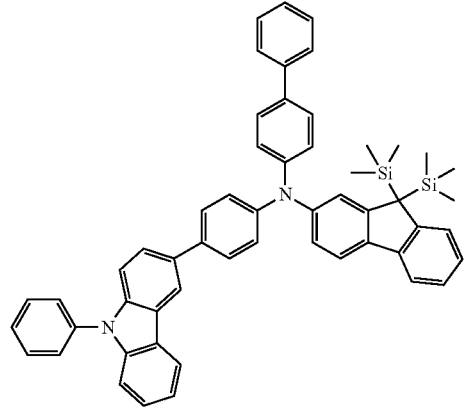
No. 84
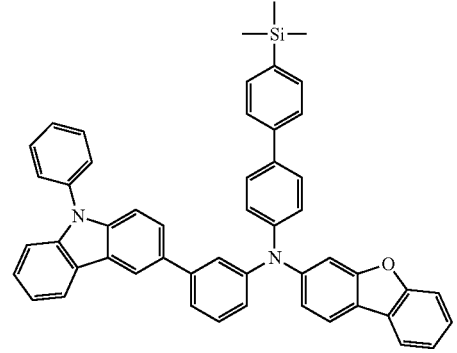

No. 85
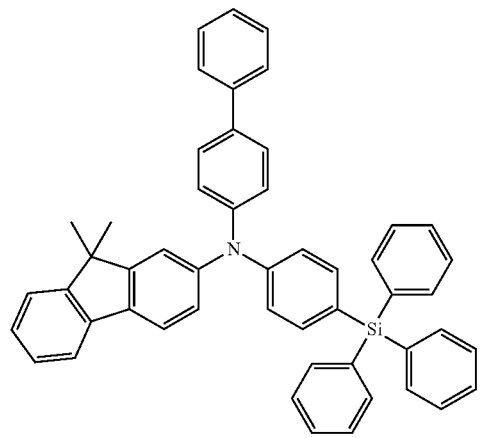
[Formula 38]
No. 86
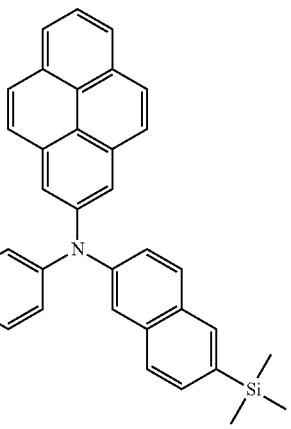
No. 87
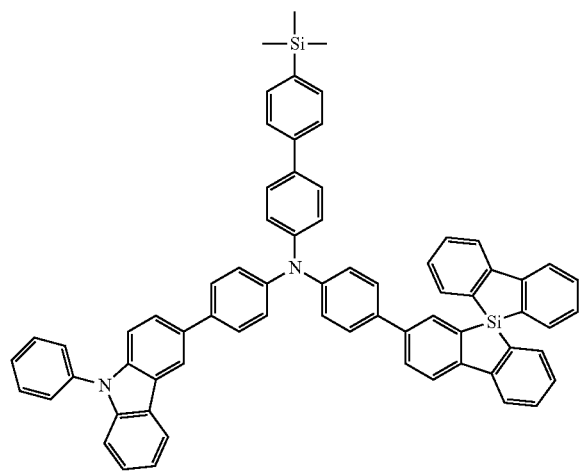
[Formula 39]
No. 88
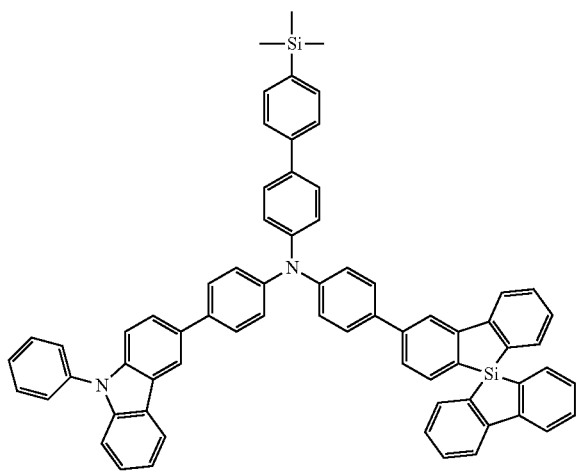
No. 89
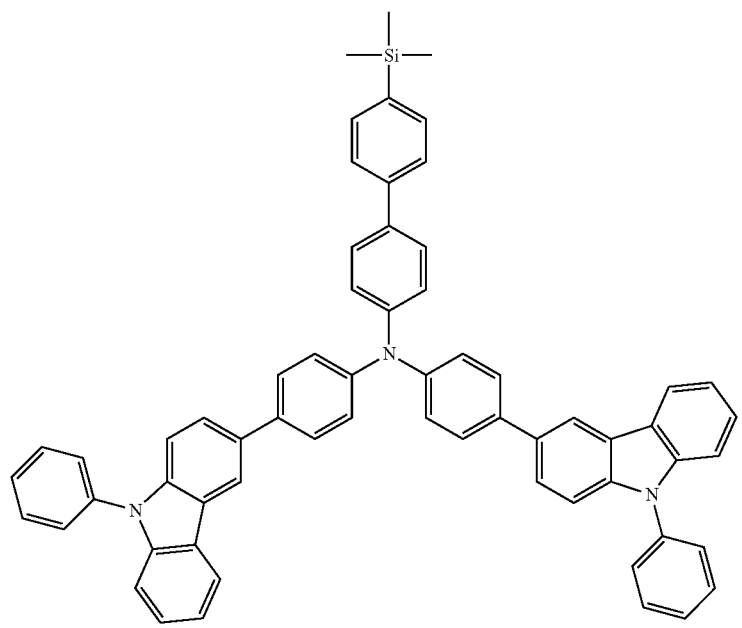

No. 90
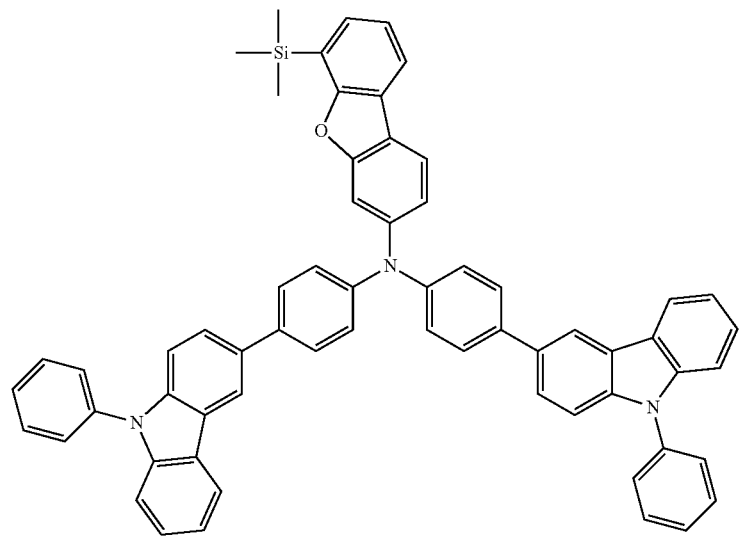
No. 91
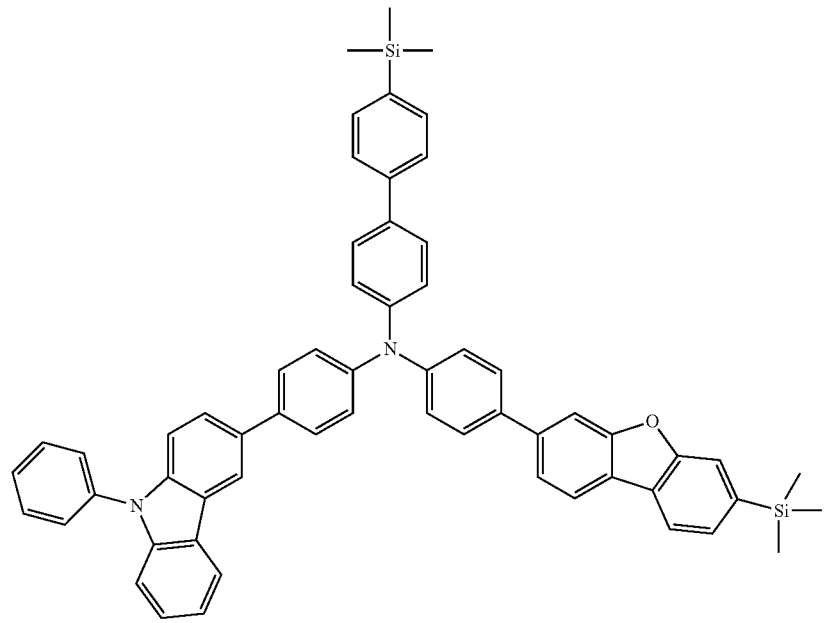

-continued
No. 92
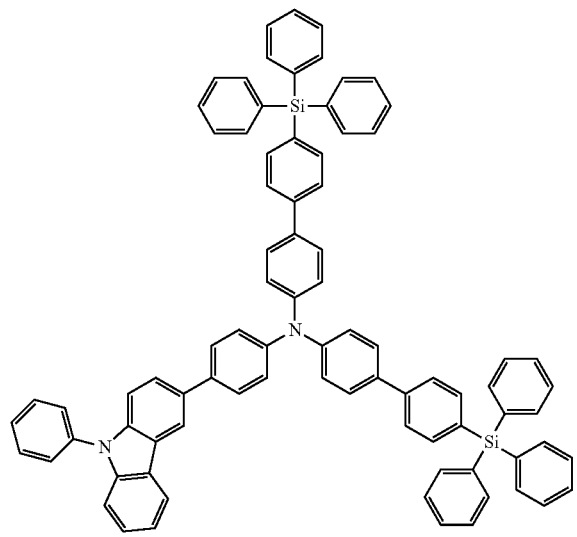
No. 93
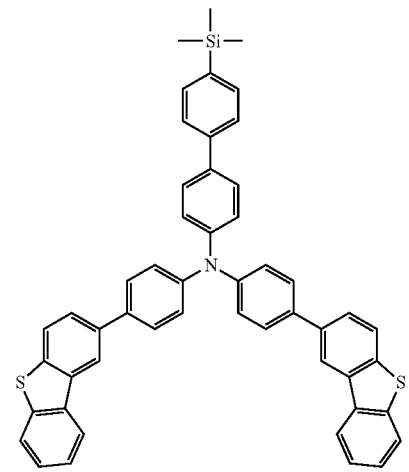
No. 94
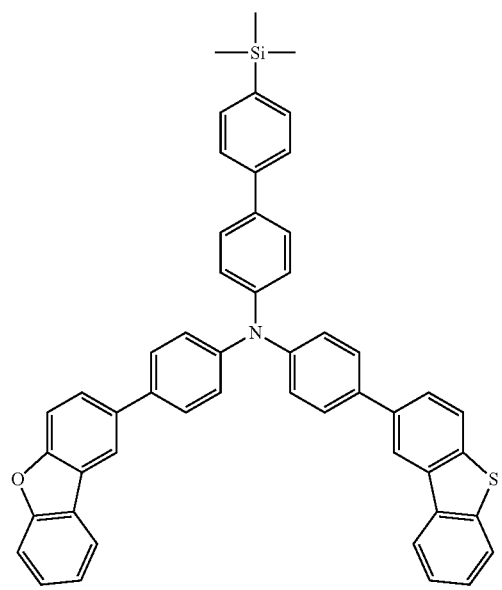
No. 95
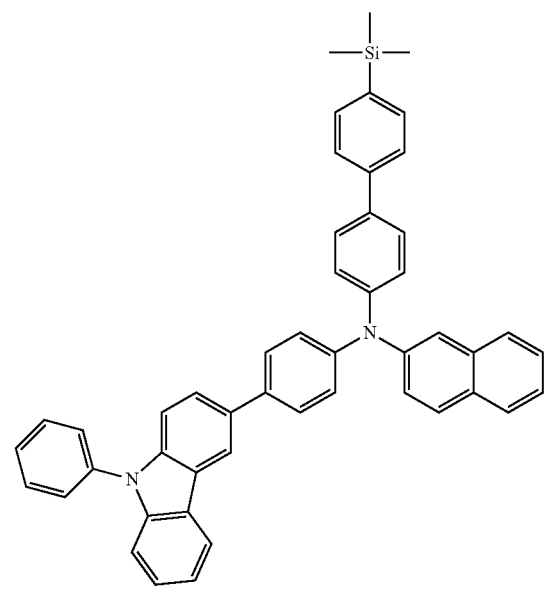
No. 96
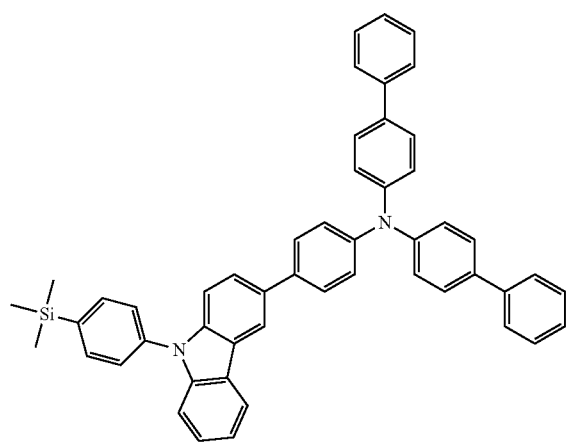
No. 97
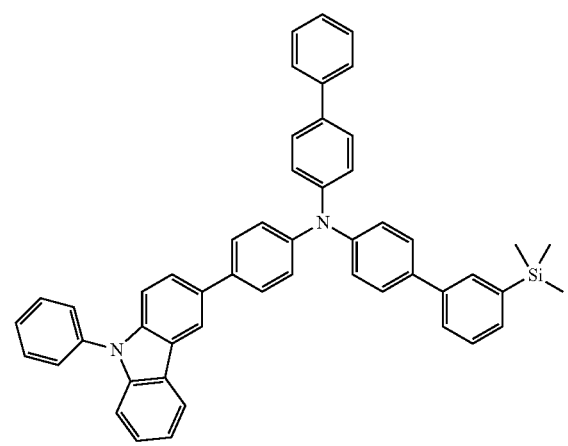

No. 98
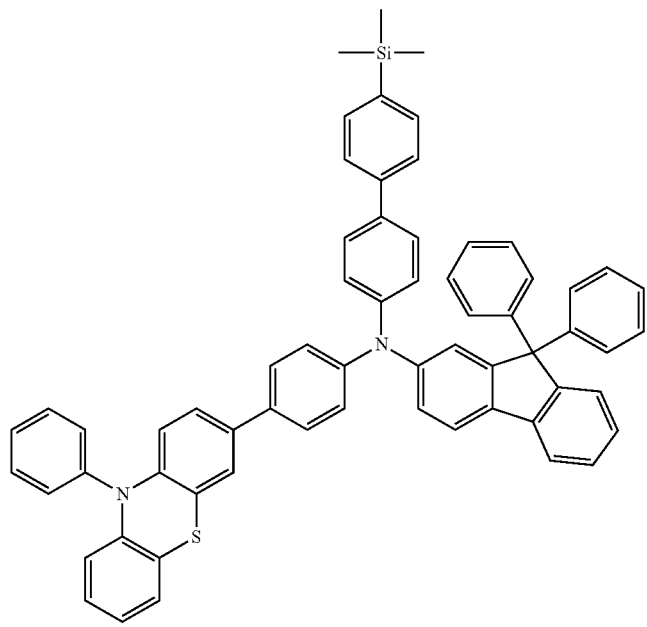
[Formula 43]
No. 99
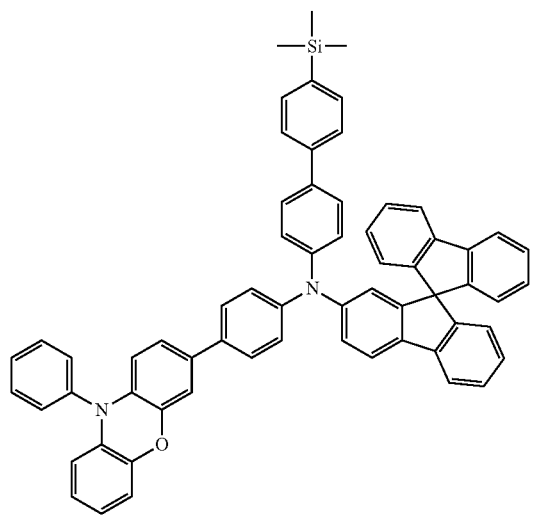
No. 100
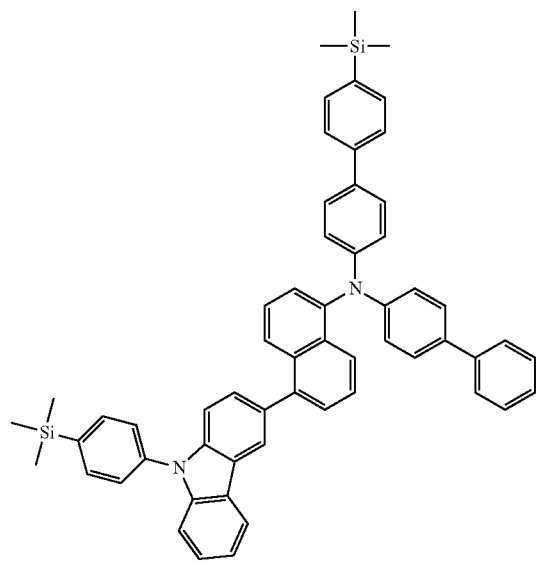

No. 101
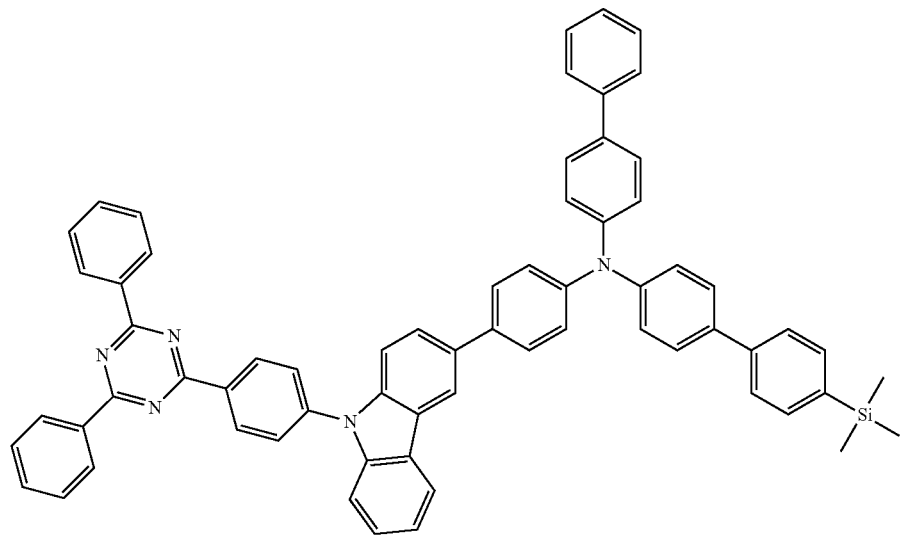
[Formula 44]
No. 102  No. 103
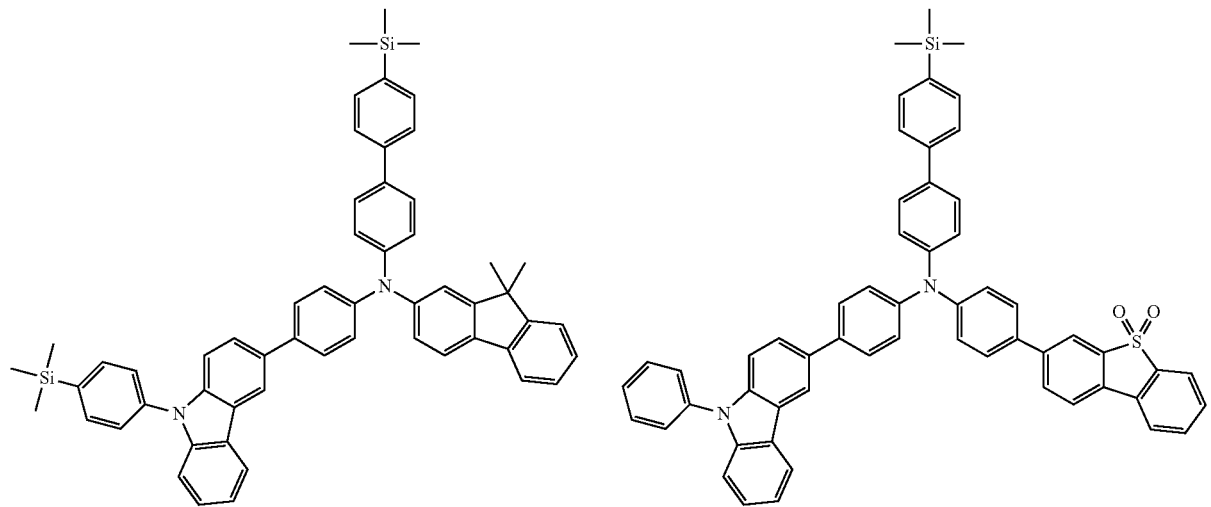

[Formula 45]
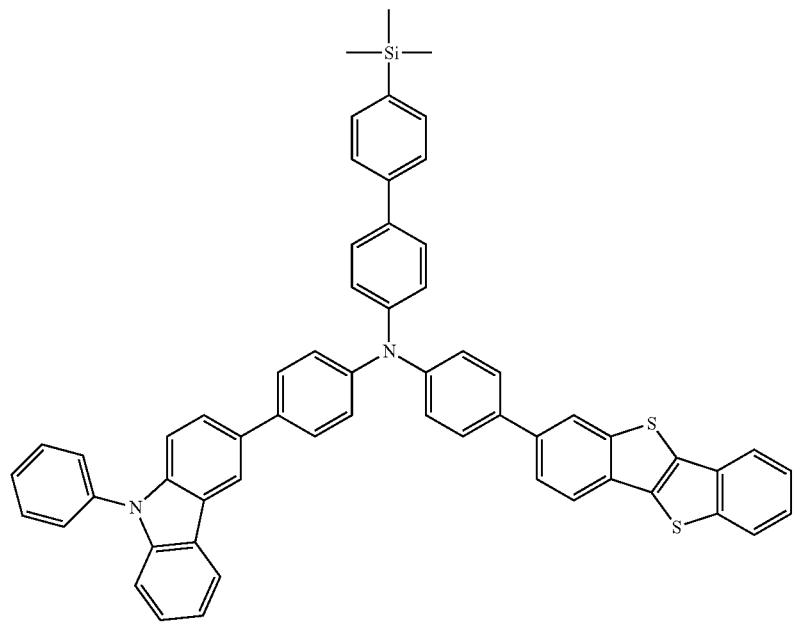
No. 104
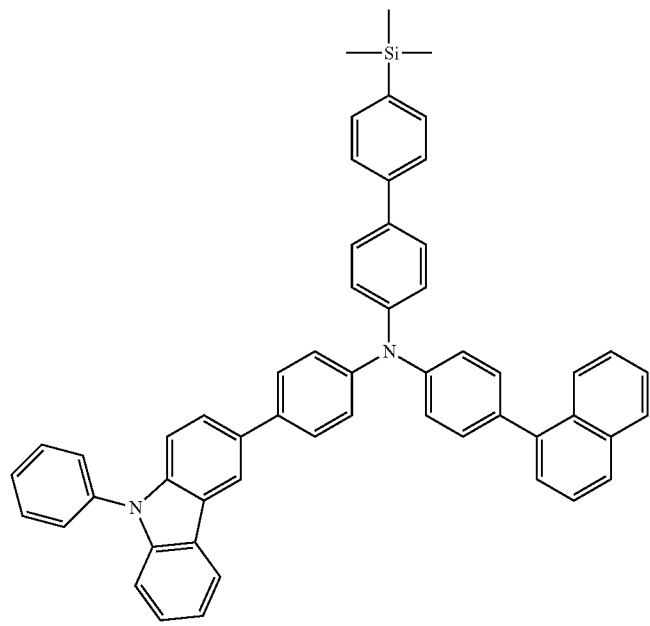
No. 105

[Formula 46]
No. 106
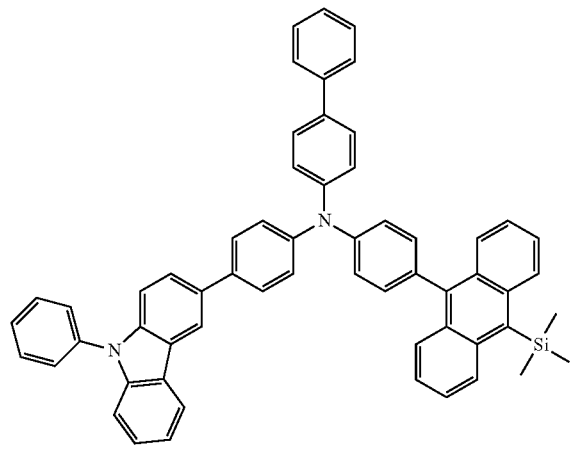
No. 107
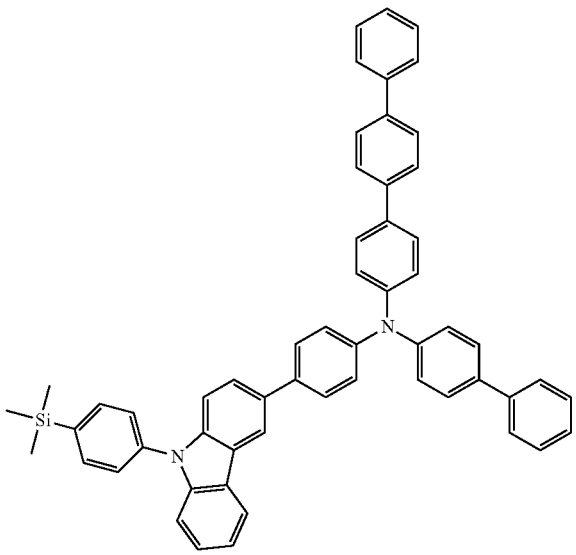
[Formula 47]
No. 108
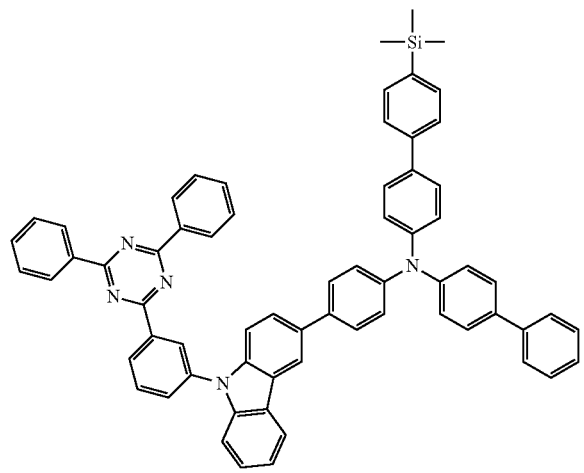
No. 109
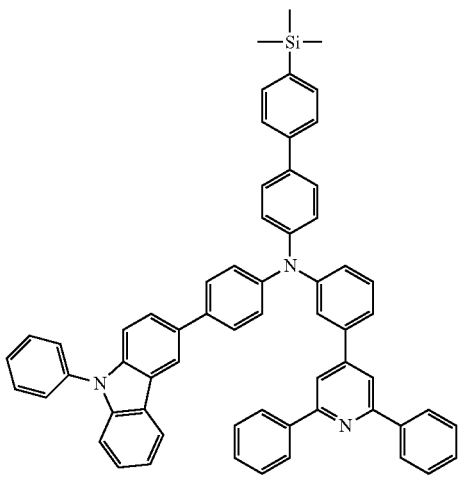

[Formula 48]

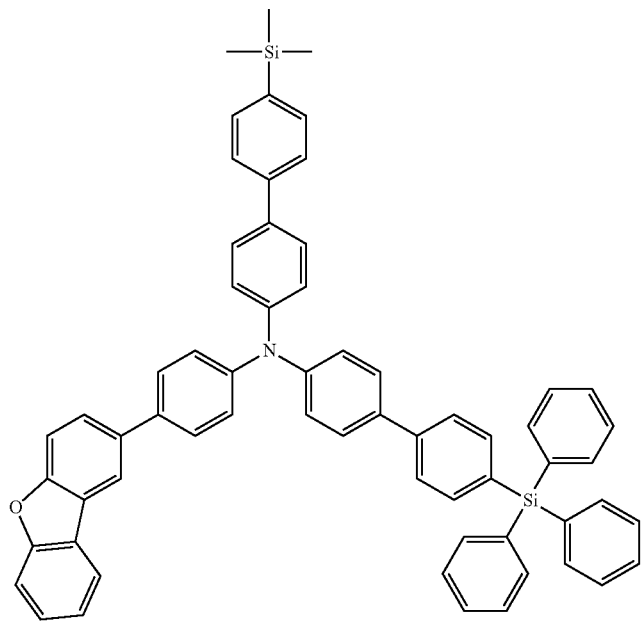

No. 110

The amine derivative having a silyl group according to an example embodiment represented by compound (1) may include, for example, the above compounds 1, 2, 3, 4, 5, 6, 8, 15, 16, 17, 18, 19, 20, 21, 22, 23, 24, 25, 26, 27, 28, 29, 30, 31, 32, 37, 38, 40, 42, 44, 45, 46, 49, 50, 53, 54, 55, 56, 57, 59, 60, 61, 62, 63, 64, 74, 77, 79, 85, 87, 88, 89, 92, 96, 98, 101, 102, 107, and 110. In an example embodiment, the amine derivative may include, for example, the above compounds 1, 2, 3, 4, 6, 15, 16, 17, 18, 19, 20, 21, 22, 23, 24, 25, 26, 27, 28, 29, 30, 31, 32, 37, 40, 44, 45, 46, 49, 53, 54, 55, 56, 57, 59, 60, 61, 62, 63, 77, 85, 87, 88, 89, 96, 101, 102, 107, and 110.

The above amine derivatives having a silyl group according to an example embodiment may be used as the materials for the organic EL device. In the amine derivative having a silyl group according to an example embodiment represented by general formula (I), at least one among the substituted or unsubstituted aryl group or the substituted or unsubstituted heteroaryl group of $Ar^1$, $Ar^2$, and $Ar^3$, connected to the nitrogen atom (N) of an amine or a linker (L) may be substituted with the substituted or unsubstituted silyl group exhibiting strong electron durability. The amine derivative having a silyl group according to an example embodiment may be stable with respect to the electrons and may be used as a material for the organic EL device, e.g., as the material of a hole transport layer adjacent to an emission layer. By using the amine derivative having a silyl group according to an example embodiment as the material of the hole transport layer, the electron durability of the hole transport layer may be improved, and the deterioration of a hole transport material due to the electrons invading the hole transport layer may be restrained, which may help realize an organic EL device having long life.

In addition, the amine derivative having a silyl group according to an example embodiment may be used, for example, as the material of a hole injection layer. When the amine derivative having a silyl group is used as the material of the hole injection layer, the deterioration of the hole injection layer due to the electrons may be restrained. Therefore, the long life of the organic EL device may be realized like the case when the amine derivative having a silyl group is used as the material of the hole transport layer.

[Embodiment of Organic EL Device]

An organic EL device may have, for example, a structure as illustrated in FIG. 1.

FIG. 1 is a schematic cross-sectional view of an organic EL device 100 according to an example embodiment when an amine derivative is used as the material of the organic EL device. Referring to FIG. 1, the organic EL device 100 may include a glass substrate 102, a positive electrode 104 disposed on the glass substrate 102, a hole injection layer 106 disposed on the positive electrode 104, a hole transport layer 108 disposed on the hole injection layer 106, an emission layer 110 disposed on the hole transport layer 108, an electron transport layer 112 disposed on the emission layer 110 and a negative electrode 116 disposed on the electron transport layer 112. The electron transport layer 112 may play the role as an electron injection layer.

With respect to the hole injection layer 106 and the hole transport layer 108 constituting the organic EL device, an amine derivative according to an example embodiment may be used as at least one material among the material for the hole injection layer and the material for the hole transport layer, thereby increasing the life of the organic EL device.

As described above, the amine derivative having a silyl group according to an example embodiment may provide electron durability, and may be used as the material of the hole transport layer or the material of the hole injection layer of the organic EL device. According to another example embodiment, the amine derivative having a silyl group according to an embodiment may be used as a host material in an emission layer.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

With respect to the amine derivative having a silyl group, synthetic examples of the above compounds 1, 3, 61, and 63 will be explained herein below.

[Synthesis of Compound 1]

In the following Formula 49, a synthetic process of compound 1 of the amine derivative having a silyl group according to an example embodiment is illustrated.

Compound 1 according to an example embodiment was synthesized by the following method.

Into a reaction vessel, compound A (1.57 g, 4.33 mmol), compound B (1.50 g, 3.61 mmol), $Pd_2$(dibenzylideneacetone)$_3$·$CHCl_3$ (0.37 g, 36 mmol), and toluene (36 mL) were added. Then, tri(t-butyl)phosphine (0.93 mL, 1.44 mmol, 1.56 M) and sodium t-butoxide (1.04 g, 10.8 mmol) were added. The inside of the reaction vessel was purged with nitrogen gas, and the reactant was stirred at 80° C. for 4 hours. After cooling, water was added into the reactant, and an organic layer was extracted. The organic layer thus obtained was dried using anhydrous magnesium sulfate, and filtered, and the filtrate was concentrated by using a rotary evaporator. The crude product thus obtained was purified by means of a silica gel column chromatography (developing solvent: dichloromethane/hexane), and the solid thus obtained was recrystallized using toluene/hexane to obtain 2.26 g of the target product of compound 1 as a solid of a white powder. The yield was 90% (FAB-MS: $C_{51}H_{41}NSi$, measured value 695).

[Synthesis of Compound 3]

In the following Formula 50, a synthetic process of compound 3 of the amine derivative according to an example embodiment is illustrated.

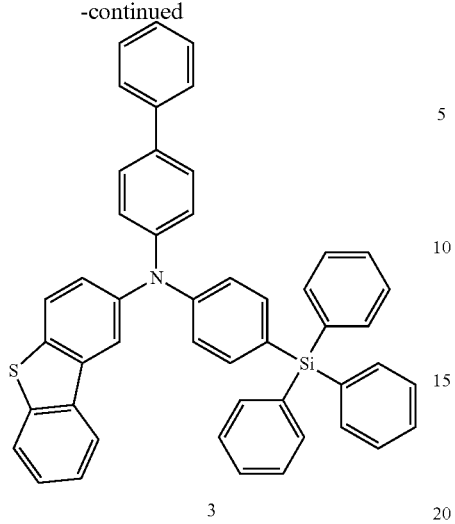

3

Compound 3 according to an example embodiment was synthesized by the following method.

Into a reaction vessel, compound C (1.52 g, 4.33 mmol), compound B (1.50 g, 3.61 mmol), $Pd_2$(dibenzylideneacetone)$_3$·$CHCl_3$ (0.37 g, 36 mmol), and toluene (36 mL) were added. Then, tri(t-butyl)phosphine (0.93 mL, 1.44 mmol, 1.56 M) and sodium t-butoxide (1.04 g, 10.8 mmol) were added. The inside of the reaction vessel was purged with a nitrogen gas, and the reactant was stirred at 80° C. for 4 hours. After cooling, water was added into the reactant, and an organic layer was extracted. The organic layer thus obtained was dried using anhydrous magnesium sulfate, and filtered, and the filtrate was concentrated by using a rotary evaporator. The crude product thus obtained was purified by means of a silica gel column chromatography (developing solvent: dichloromethane/hexane), and the solid thus obtained was recrystallized using toluene/hexane to obtain 1.00 g of the target product of compound 3 as a solid of a white powder. The yield was 40% (FAB-MS: $C_{48}H_{35}NSSi$, measured value 685).

[Synthesis of Compound 61]

In the following Formula 51, a synthetic process of compound 61 of the amine derivative according to an example embodiment is illustrated.

[Formula 51]

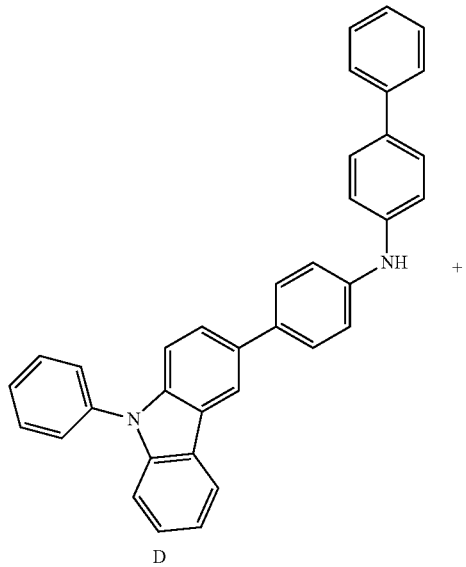

D

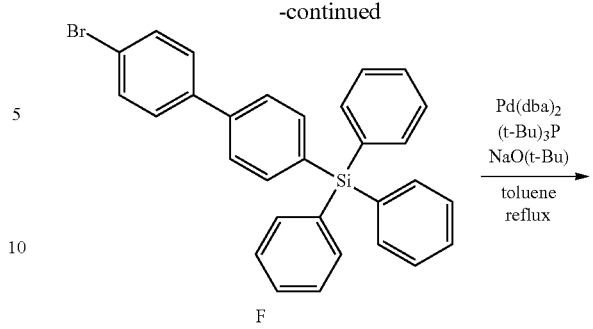

F

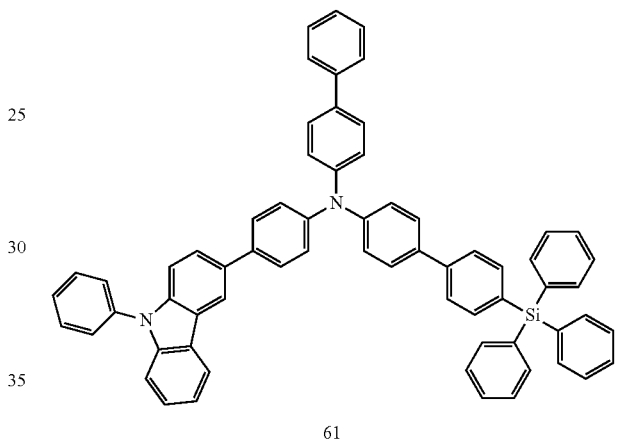

61

Compound 61 according to an example embodiment was synthesized by the following method.

Into a reaction vessel, compound D (0.70 g, 1.44 mmol), compound F (0.71 g, 1.44 mmol), $Pd(dba)_2$ (0.04 g, 0.07 mmol), and toluene (36 mL) were added. Then, tri(t-butyl)phosphine (0.14 mL, 0.28 mmol, 2.00 M) and sodium t-butoxide (0.21 g, 2.16 mmol) were added. The inside of the reaction vessel was purged with a nitrogen gas, and the reactant was refluxed for 6 hours while stirring. After cooling, water was added into the reactant, and an organic layer was extracted. The organic layer thus obtained was dried using anhydrous magnesium sulfate, and filtered, and the filtrate was concentrated by using a rotary evaporator. The crude product thus obtained was purified by means of a silica gel column chromatography (developing solvent: toluene/hexane), and the solid thus obtained was recrystallized using dichloromethane/hexane to obtain 1.15 g of the target product of compound 61 as a solid of a white powder. The yield was 89% (FAB-MS: $C_{66}H_{48}N_2Si$, measured value 897).

[Synthesis of Compound 63]

In the following Formula 52, a synthetic process of compound 63 of the amine derivative according to an example embodiment is illustrated.

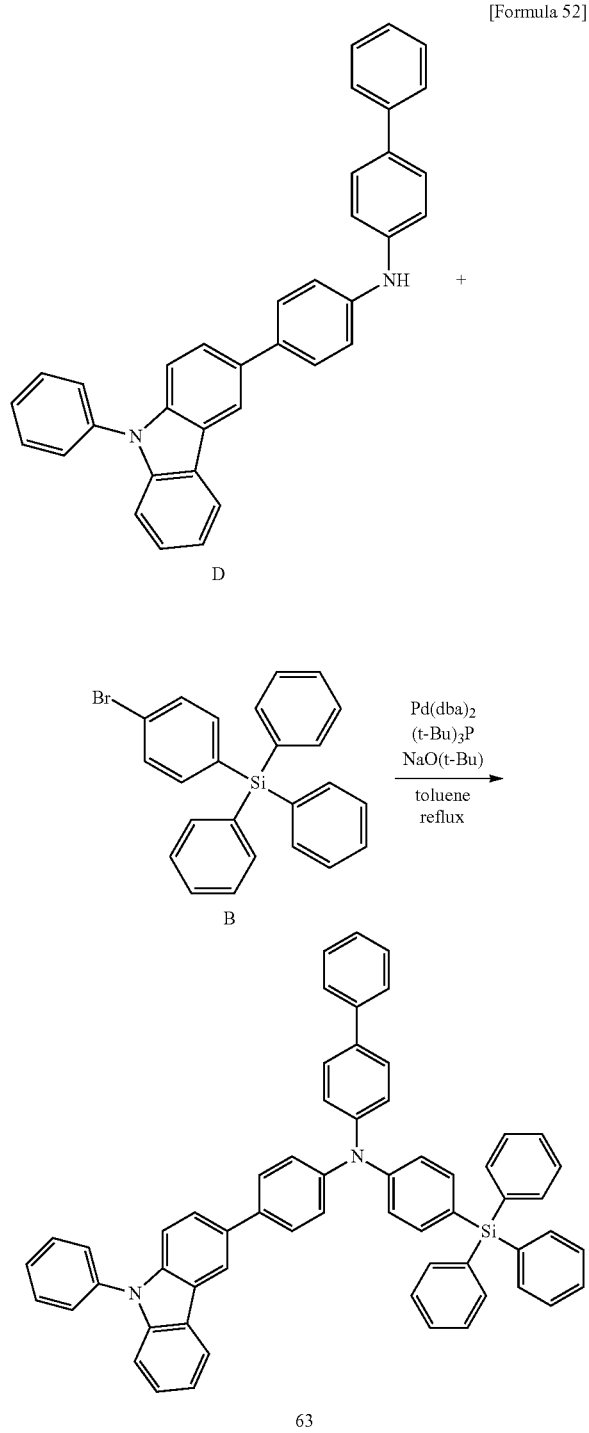

Compound 63 according to an example embodiment was synthesized by the following method.

Into a reaction vessel, compound D (1.00 g, 2.06 mmol), compound B (0.85 g, 2.06 mmol), Pd(dba)$_2$ (0.06 g, 0.10 mmol), and toluene (10 mL) were added. Then, tri(t-butyl) phosphine (0.03 mL, 0.06 mmol, 2.00 M) and sodium t-butoxide (0.30 g, 3.08 mmol) were added. The inside of the reaction vessel was purged with a nitrogen gas, and the reactant was refluxed for 4 hours while stirring. After cooling, water was added into the reactant, and an organic layer was extracted. The organic layer thus obtained was dried using anhydrous magnesium sulfate, and filtered, and the filtrate was concentrated by using a rotary evaporator. The crude product thus obtained was purified by means of a silica gel column chromatography (developing solvent: toluene/hexane), and the solid thus obtained was recrystallized using dichloromethane/hexane to obtain 1.59 g of a target product as a solid of a white powder. The yield was 94% (FAB-MS: C60H44N$_2$Si, measured value 821).

[Organic EL Device]

Hereinafter, an organic EL device of Example 1, in which the compound 1 is used as the material of the organic EL device according to an example embodiment in a hole transport layer will be explained.

[Manufacturing Method of Organic EL Device According to Example 1]

The organic EL device of Example 1 according to an example embodiment was manufactured by a vacuum deposition method according to the following order. First, the surface of an ITO-glass substrate patterned and washed in advance was treated with ozone. The thickness of the ITO layer was about 150 nm. After the ozone treatment, a layer was formed using 4,4',4''-tris(N,N-(2-naphthyl)phenylamino)triphenylamine (2-TNATA, thickness of about 60 nm) as a hole injection material on the ITO layer.

After that, a layer was formed using compound 1 according to an example embodiment as a hole transport material, and another layer was formed by co-depositing a layer obtained by doping 1,1,4,4-tetraphenyl-1,3-butadiene (TPB) with the ratio of 3% with respect to 9,10-di(2-naphthyl) anthracene (β-ADN) as an emission material (25 nm).

Then, a layer was formed using tris(8-quinolinato)aluminum (Alq$_3$) as an electron transport material (25 nm), and lithium fluoride (LiF) as an electron injection material (1.0 nm) and aluminum as a negative electrode (100 nm) were deposited in order, thereby manufacturing an organic EL device 200.

In Example 2, an organic EL device was manufactured by performing the same method as described in Example 1 except for using compound 3 instead of compound 1 used in Example 1.

In Example 3, an organic EL device was manufactured by performing the same method as described in Example 1 except for using compound 61 instead of compound 1 used in Example 1.

In Example 4, an organic EL device was manufactured by performing the same method as described in Example 1 except for using compound 63 instead of compound 1 used in Example 1.

In Comparative Examples 1 and 2, organic EL devices were manufactured by performing the same method as described in Example 1 except for using the following compound 53 for Comparative Example 1 and the following compound 54 for Comparative Example 2 instead of compound 1 used in Example 1 as the compounds forming the materials of the hole transport layers of the organic EL devices.

[Formula 53]

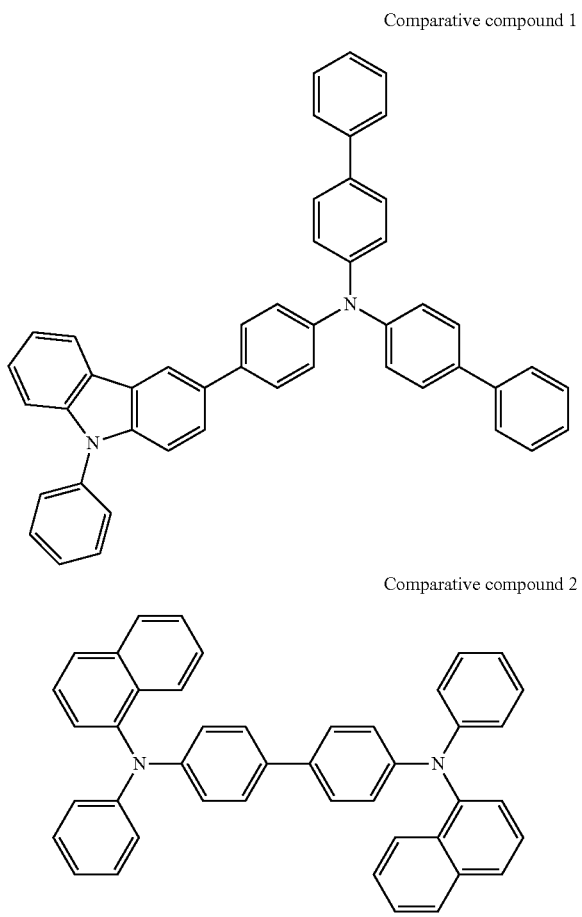

Comparative compound 1

Comparative compound 2

Figure 2:
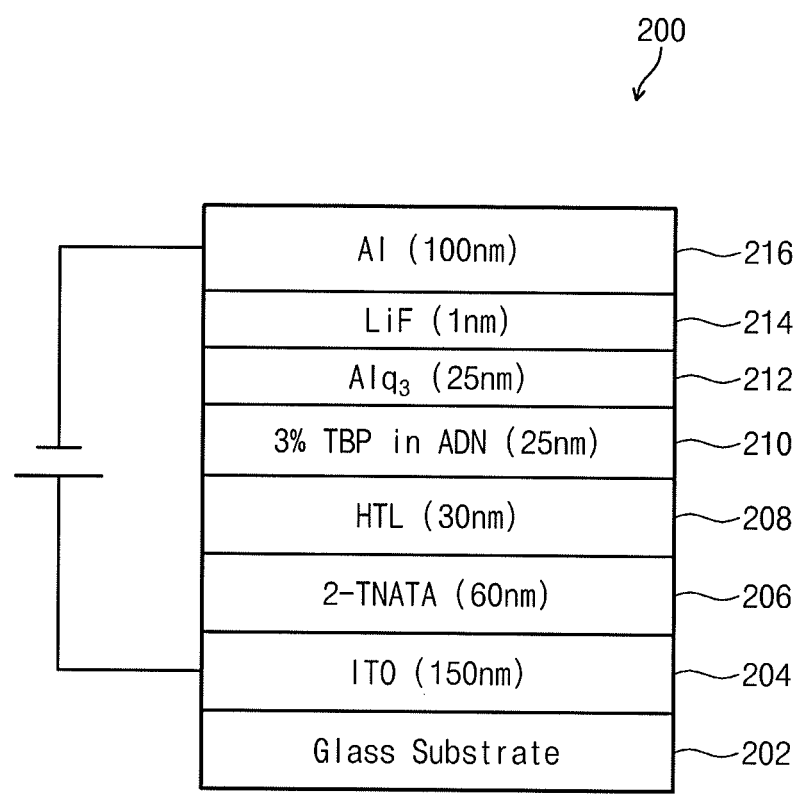
FIG. 2 illustrates a schematic diagram of an organic EL device manufactured by using an organic EL material according to an example embodiment.

The schematic diagram of the organic EL device 200 thus manufactured in Examples 1 to 4 and Comparative Examples 1 and 2 is illustrated in FIG. 2. The organic EL device 200 includes a positive electrode 204, a hole injection layer 206 disposed on the positive electrode 204, a hole injection layer 206 disposed on the positive electrode 204, a hole transport layer 208 disposed on the hole injection layer 206, an emission layer 210 disposed on the hole transport layer 208, an electron transport layer 212 and an electron injection layer 214 disposed on the emission layer 210, and a negative electrode 216 disposed on the electron injection layer 214.

The device performance of the organic EL device 200 thus manufactured in Examples 1 to 4 and Comparative Examples 1 and 2, is illustrated in the following Table 1.

TABLE 1

| | Hole transport material | Voltage (V) | Current efficiency (cd/A) (@10 mA/cm$^2$) | Life (hr) (@1000 cd/m$^2$) |
| --- | --- | --- | --- | --- |
| Example 1 | Compound 1 | 7.1 | 6.4 | 1,700 |
| Example 2 | Compound 13 | 7.0 | 6.3 | 1,800 |
| Example 3 | Compound 61 | 6.7 | 6.9 | 2,000 |
| Example 4 | Compound 63 | 6.8 | 6.7 | 1,900 |
| Comparative Example 1 | Comparative compound 1 | 7.5 | 6.2 | 1,500 |
| Comparative Example 2 | Comparative compound 2 | 8.1 | 5.3 | 1,200 |

In addition, the electroluminescent properties of the organic EL device 200 thus manufactured were evaluated by using a C9920-11 luminance alignment property measuring apparatus of Hamamatsu Photonics.

According to Table 1, the organic EL devices of Examples 1 to 4 have longer life than that of the organic EL devices of Comparative Examples 1 and 2.

By way of summation and review, an organic electroluminescence device (herein referred to as an organic EL device) may include a multiple layers of an emission layer and other layers such as a carrier (hole, electron) transport layer.

As described above, embodiments relate to an amine derivative that may be used as an organic electroluminescence material, e.g., an organic electroluminescence material such as a hole transport material, etc., and an organic electroluminescence device using the same.

When light is emitted by the recombination of holes and electrons near the interface of an emission layer and a hole transport layer, electrons that could not participate in the recombination may invade the hole transport layer and damage a hole transport material, which may deteriorate a device. According to an example embodiment, the deterioration mechanism of a device caused by electrons invading the hole transport layer may be restrained, and an organic EL device of which life is increased, and an organic EL material for realizing the organic EL device may be provided.

According to an example embodiment, an organic EL device having improved life, and an organic EL material for realizing thereof may be provided.

The amine derivative having a silyl group according to an example embodiment includes the silyl group, and may provide electron durability. The amine derivative may be used for a material for conducting stable hole transport with respect to electrons. By using the amine derivative having a silyl group according to an embodiment, the deterioration of a device due to electrons invading a hole transport layer may be restrained, and the life of the device may be increased.

Examples of using the amine derivative having a silyl group according to an example embodiment as the hole transport material of the organic EL device are described above. In addition, the amine derivative having a silyl group according to an example embodiment may be used in other light-emitting devices or light-emitting apparatuses. In addition, the organic EL device illustrated in FIGS. 1 and 2 corresponds to an organic EL display of a passive matrix driving type, but an organic EL display of an active matrix driving type may also be formed.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An amine derivative represented by compound (1) of the following Formula 1:

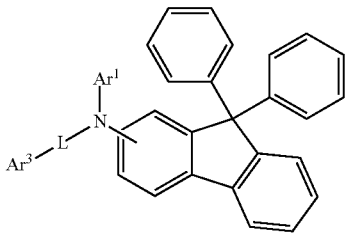

[Formula 1]

wherein,
$Ar^1$ is unsubstituted group having 6 to 18 carbon atoms forming a ring,
$Ar^3$ is a substituted aryl group, substituted with a triarylsilyl group of 18 to 30 carbon atoms forming a ring or a trialkyl silyl group of 3 to 18 carbon atoms, and
L is a direct bond, a substituted or unsubstituted arylene group, or a substituted or unsubstituted heteroarylene group.

2. The amine derivative as claimed in claim 1, wherein $Ar^1$ is an unsubstituted phenyl group.

3. The amine derivative as claimed in claim 1, wherein L is a linker or an arylene group having 6 to 14 carbon atoms.

4. A material for an organic electroluminescence device, the material comprising the amine derivative as claimed in claim 1.

5. A hole transport material for an organic electroluminescence device, the hole transport material comprising the amine derivative as claimed in claim 1.

6. An organic electroluminescence device comprising at least an emission layer and a hole transport layer disposed between a negative electrode and a positive electrode, the hole transport layer including the amine derivative as claimed in claim 1.

7. The amine derivative as claimed in claim 1, wherein $AR^3$ is substituted with a substituted or unsubstituted triphenyl silyl, or a substituted or unsubstituted trimethyl silyl.

* * * * *